United States Patent
Sato et al.

(10) Patent No.: US 7,736,376 B2
(45) Date of Patent: Jun. 15, 2010

(54) LIVING BODY WALL FIXING TOOL USED IN ENDOSCOPE

(75) Inventors: Masatoshi Sato, Yokohama (JP); Toshihiro Shizuka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 918 days.

(21) Appl. No.: 11/481,354

(22) Filed: Jul. 5, 2006

(65) Prior Publication Data

US 2008/0319257 A1    Dec. 25, 2008

(51) Int. Cl.
*A61B 17/08* (2006.01)
(52) U.S. Cl. ...................................... 606/213
(58) Field of Classification Search ........... 606/139, 606/213, 224
See application file for complete search history.

(56) References Cited

U.S. PATENT DOCUMENTS

| | | | | |
|---|---|---|---|---|
| 5,545,178 A | * | 8/1996 | Kensey et al. | 606/213 |
| 6,423,087 B1 | * | 7/2002 | Sawada | 606/213 |
| 2004/0186514 A1 | | 9/2004 | Swain et al. | |
| 2005/0137612 A1 | * | 6/2005 | Assell et al. | 606/108 |

FOREIGN PATENT DOCUMENTS

| | | |
|---|---|---|
| JP | 2001-46514 | 2/2001 |
| WO | WO 02/094108 A2 | 11/2002 |

* cited by examiner

*Primary Examiner*—Julian W Woo
*Assistant Examiner*—Christina Lauer
(74) *Attorney, Agent, or Firm*—Scully, Scott, Murphy & Presser, P.C.

(57) ABSTRACT

A living-wall fixing tool for use with endoscopes, including first and second fixing members, first and second cord like members, an elastic stopper, and a slackening means. The first fixing member is to be inserted into a second organ through a hole formed through first and second organs. The second fixing member is to be detained in the first organ. The stopper is slidably mounted on the first cord-like member. The slackening means slackens the first cord-like member. When the slackening means is operated, the second cord-like member is pulled, whereby the first fixing member is pulled into the first organ through the hole.

7 Claims, 15 Drawing Sheets

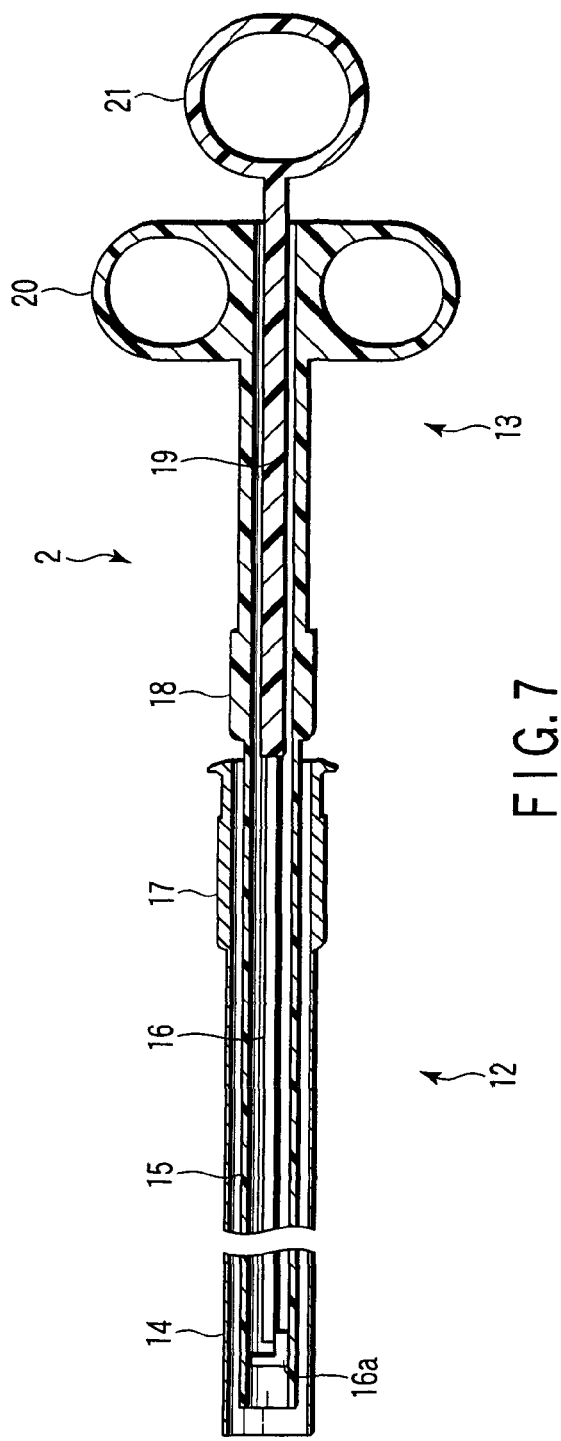
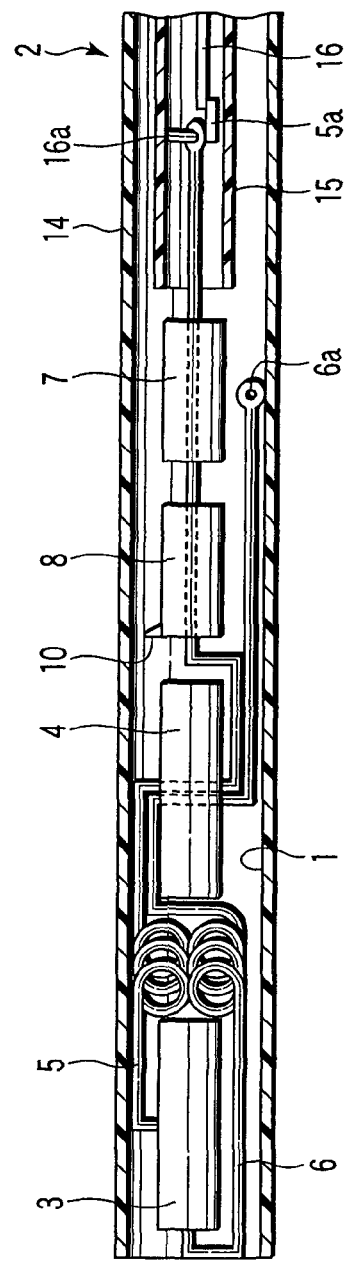
FIG. 7
FIG. 8

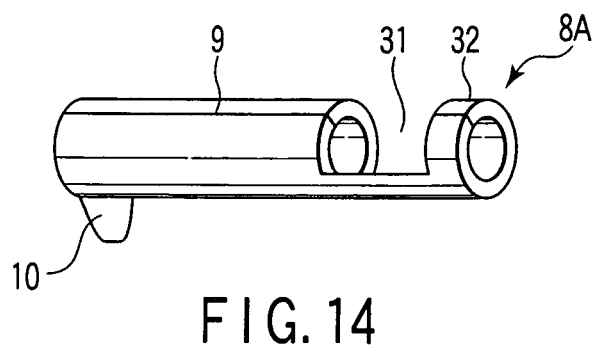
F I G. 14
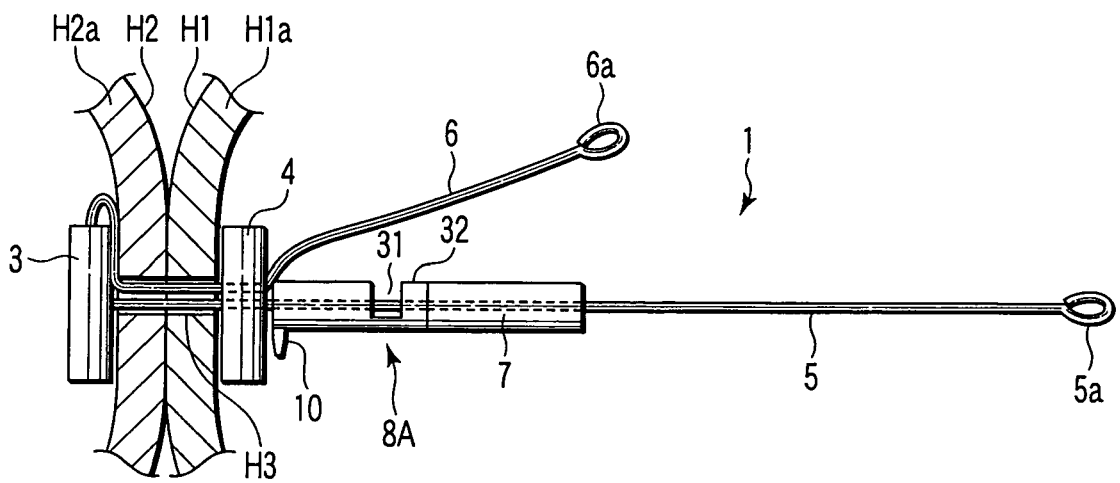
F I G. 15

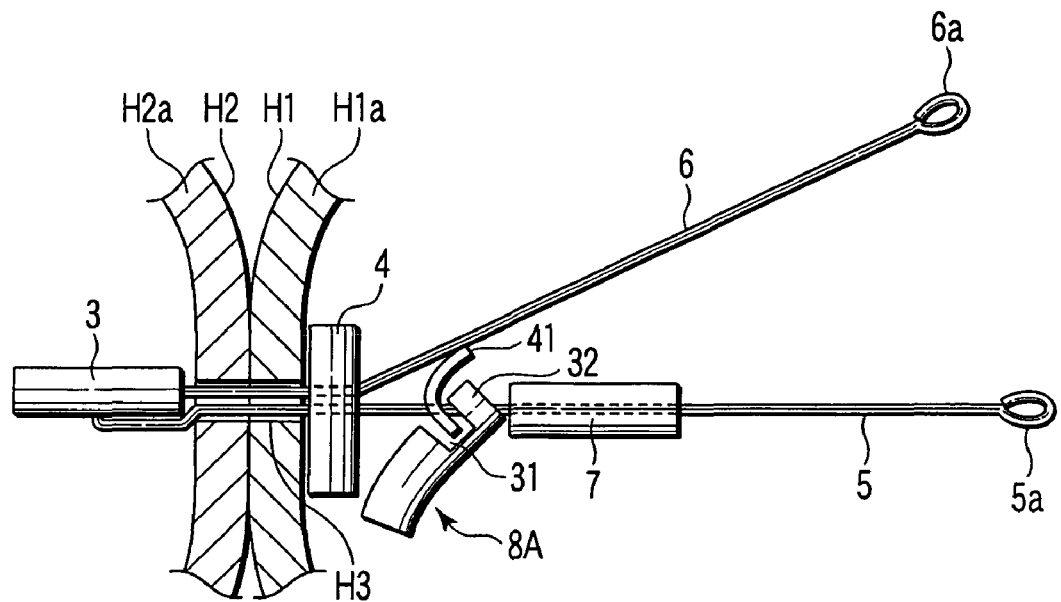
F I G. 22
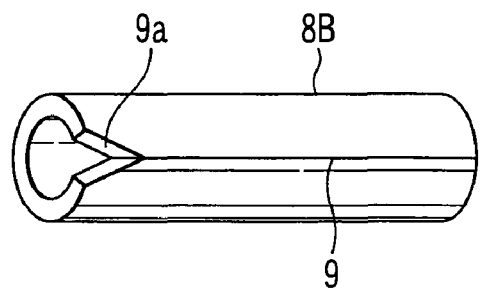
F I G. 23

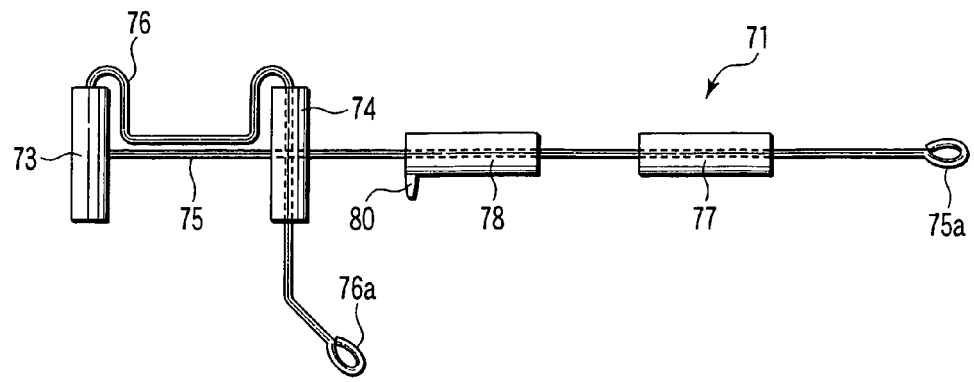
F I G. 37
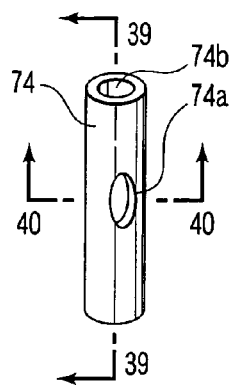
F I G. 38
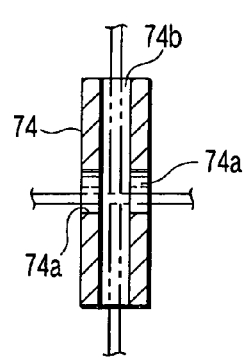
F I G. 39
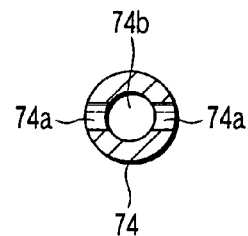
F I G. 40
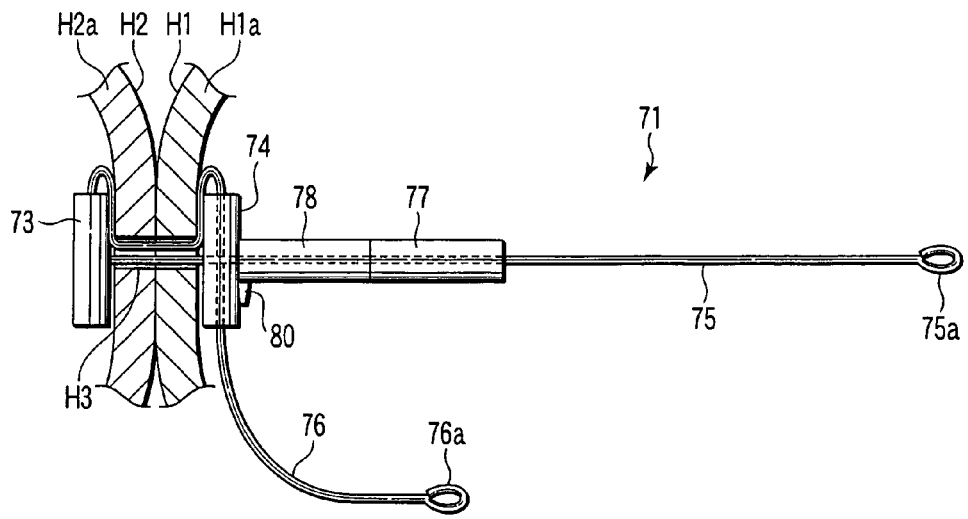
F I G. 41

LIVING BODY WALL FIXING TOOL USED IN ENDOSCOPE

BACKGROUND OF THE INVENTION

Hitherto, percutaneous transhepatic cholangiodrainage (PTBD) that may damage the human body surface has been generally performed to cure obstructive jaundice, i.e., the blockade of the bile duct, which develops due to a pathological change. In recent years, endoscopic retrograde biliary drainage (ERBD) or endoscopic naso biliary drainage (ENBD) has come to be performed, thanks to the progress in the endoscope technology. In ERBD, a endoscope channel is inserted into the bile duct through the patient's mouth, and a stent tube is inserted into the bile duct through the channel and is left in the bile duct. The stent tube thus left opens the bile duct, enabling the bile to flow through the bile duct.

As time passes while the stent tube remains left in the bile duct, the components of the bile adhere to the inner surface of the tube. If the stent tube is clogged, the stent tube must be pulled out, and a new stent tube must be inserted into the bile duct, by using a endoscope.

Jpn. Pat. Appln. KOKAI Publication No. 2001-46514 discloses a method of treating jaundice, in which anastomosis is performed by using no stent tubes, in order to connect the choledochus to the duodenum. In this treatment of jaundice, a fixing tool is used in combination with endoscopes, clamping and holding the walls of these two organs, and the distal end of the endoscope is located at the position where the choledochus lies most close to the duodenum. Subsequently, a resection instrument, such as a cautery knife, is guided to the position through the endoscope channel. By using the knife, perforation is performed on both the duodenum and the choledochus. To form a natural stoma between the duodenum and the choledochus, these organs must be kept held together for a prescribed time. Once a natural stoma is formed, the fixing tool is no longer necessary. The holding instrument, which is foreign matter, should then be removed from the patient.

BRIEF SUMMARY OF THE INVENTION

A living-wall fixing tool for use with endoscopes, according to an embodiment of this invention, is designed to be detained in a living body by using a detention device inserted into the living body through the channel of an endoscope and to clamp the walls of the first and second organs in the living body, the endoscope being inserted into the first organ and not inserted into the second organ. The living-wall fixing tool comprises: first and second fixing members which are shaped like a shaft, the first fixing member being configured to be inserted into the second organ through a hole formed in a junction between a first living wall of the first organ and a second living wall of the second organ, and the second fixing member being configured to be arranged in the first organ, not inserted into the hole; first and second cord-like members which are to be used in combination with the two fixing members, the first cord-like member having a distal end part connected to the first fixing member and a proximal part extending away from the first fixing member through the second fixing member, and the second cord-like member having a distal end part connected to an end of the first fixing member and a proximal part extending away from the first fixing member through the second fixing member; an elastic stopper which is sildably mounted on the first cord-like member and which is connected to the first cord-like member when the first cord-like member is pulled, causing the first and second fixing member to clamp the first and second living walls; and slackening means for slackening the first cord-like member, the slackening means being configured to pull the second cord-like member when the first fixing member is pulled into the first organ through the hole.

Preferably, the first fixing member is constituted by a straight bar which has holes in a middle part, the holes extending at right angles to an axis of the straight bar, the first cord-like member is constituted by a first cord, and parts of the first cord, which project from the holes, are pulled to a proximal end of the first cord, applying a tension, thereby to fix the distal end of the first cord-like member to the first fixing member.

Preferably, the first fixing member is constituted by a straight tube, the second cord-like member is a second cord, the second cord-like member has a stopper member at an end part which protrudes from the tube while the second cord remains movably inserted in the tube and which has diameter larger than an inside diameter of the tube, and fixing means is provided, which is configured to pull the second cord toward a proximal end of the second cord-like member, thereby applying a tension and bringing the stopper member fix into abutment on the first fixing member, thereby to fix the distal end of the first cord-like member to the first fixing member.

Preferably, the slackening means has a tubular spacer member to be slidably inserted into the first cord-like member, and the spacer member can be released from the first cord-like member.

Preferably, the spacer member has a slit made in the tube wall and a tag formed on the wall and facing away from the slit, the slit extending in an axial direction of the tube, and the spacer member is released from the first cord-like member through the slit when the tag is pulled.

Preferably, the spacer member has a tag separated from a main body of the spacer member and slidably mounted on the first cord-like member, and the spacer member is released from the first cord-like member through the slit when the tag is pulled.

Preferably, the spacer member is at least half as long as the first fixing member as measured in the axial direction of the first fixing member.

Preferably, the spacer member has, at an end of the slit, a guiding part for guiding the first cord-like member.

Preferably, the spacer member has a ring-shaped part that has no slits, at a position in the axial direction of the tube, and the part of the spacer member, other than the ring-shaped part, can be released from the first cord-like member through the slit.

Preferably, the slackening means has a first cord-fixing part which is located at a middle part of the first fixing member in the axial direction thereof and to which the distal end of the first cord-like member is fixed, a second cord-fixing part which is located at an end of the first fixing member and to which the distal end of the second cord-like member is fixed, and an cord insertion hole which is made in a middle part of the second fixing member in the axial direction thereof and which extends at right angles to the axial direction of the second fixing member, and the first cord-like member and the second cord-like member extend away from the first fixing member through the cord insertion hole.

Preferably, the second fixing member is a tubular member, the second cord-like member is inserted into the tubular member through the cord insertion hole and protrudes from the tubular member through an opening end of the second fixing member.

Preferably, the second fixing member is a tubular member, the second cord-like member is inserted into the tubular member through one opening end of the second fixing member and protrudes from the tubular member through the other opening end of the second fixing member.

A living-wall fixing tool for use with endoscopes, according to another embodiment of this invention, is designed to be detained in a living body by using a detention device inserted into the living body through the channel of an endoscope and to clamp the walls of the first and second organs in the living body. The endoscope is inserted into the first organ and not inserted into the second organ. The detention device comprises an insertion section to be inserted into the living body through the channel of the endoscope and a handle section arranged at a proximal end of the insertion section. The insertion section comprises an outer tube, an inner tube provided in the outer tube and capable of slide in an axial direction of the outer tube, and an operation wire provided in the inner tube, able to slide in an axial direction of the inner tube and having a hook part at a distal end. The handle section has an inner-tube operating part which makes the inner tube slide with respect to the outer tube in the axial direction of the outer tube, and a wire-operating part which makes the operation wire slide with respect to the inner tube in the axial direction of the inner tube. The living-wall fixing tool for use with endoscopes has: first and second fixing members which are shaped like a shaft, the first fixing member being configured to be inserted into the second organ through a hole formed in a junction between a first living wall of the first organ and a second living wall of the second organ, and the second fixing member being configured to be arranged in the first organ, not inserted into the hole; first and second cord-like members which are to be used in combination with the two fixing members, the first cord-like member having a distal end part connected to the first fixing member and a proximal part extending away from the first fixing member through the second fixing member, and the second cord-like member having a distal end part connected to an end of the first fixing member and a proximal part extending away from the first fixing member through the second fixing member; an elastic stopper which is sildably mounted on the first cord-like member and which is connected to the first cord-like member when the first cord-like member is pulled, causing the first and second fixing member to clamp the first and second living walls; and slackening means for slackening the first cord-like member, the slackening means being configured to pull, when operated, the second cord-like member, thereby to pull the first fixing member into the first organ through the hole. The living-wall fixing tool for use with endoscopes is configured to be drawn into the outer tube of the detention device, with the first cord-like member having the distal end engaged with the hook part. The living-wall fixing tool for use with endoscopes is configured to be pushed from the outer tube as the inner tube of the detention device is pushed, and to clamp the living walls of the first and second organs to each other.

A method of manipulating a living-wall fixing tool for use with endoscopes is provided, according to still another embodiment of this invention. The living-wall fixing tool is designed to be detained in a living body by using a detention device inserted into the living body through the channel of an endoscope and to clamp a first living wall and a second living wall, or the walls of the first and second organs in the living body, the endoscope being inserted into the first organ and not inserted into the second organ. The method comprises: a step of inserting the first fixing member of the living-wall fixing tool into the second organ through a hole formed in a junction between the first living wall and the second living wall; a step of positioning the second fixing member of the living-wall fixing tool in the first organ, without inserting the second fixing member into the first organ; a step of pulling a first cord-like member having a distal end fixed to the first fixing member, with a tubular spacer member inserted slidably in the first cord-like member, after a proximal end of the first cord-like member extends through the second fixing member away from the first fixing member and after a proximal end of a second cord-like member having a distal end fixed to an end of the first fixing member passes through the second fixing member and extends away from the first fixing member, thereby pressing a stopper onto the first cord-like member and placing the first and second living walls between the first and second fixing members, thus holding the living walls clamped together; a step of releasing the spacer member from the first cord-like member, thereby slackening the first cord-like member and moving the first cord-like member into a gap between the second fixing member and the stopper; and a step of pulling the second cord-like member after the spacer member is released from the first cord-like member, thereby moving the first cord-like member toward the first fixing member, positioning the first fixing member substantially parallel to the hole, and pulling the first fixing member through the hole into the first organ.

A method of manipulating a living-wall fixing tool for use with endoscopes is provided according to another embodiment of this invention. The living-wall fixing tool is designed to be detained in a living body by using a detention device inserted into the living body through the channel of an endoscope and to clamp a first living wall and a second living wall, or the walls of the first and second organs in the living body, the endoscope being inserted into the first organ and not inserted into the second organ. This method comprises: a step of inserting the first fixing member of the living-wall fixing tool into the second organ through a hole formed in a junction between the first living wall and the second living wall; a step of positioning the second fixing member of the living-wall fixing tool in the first organ, without inserting the second fixing member into the first organ; a step of pulling a first cord-like member having a distal end fixed to the first fixing member, after a proximal end of the first cord-like member extends through the second fixing member away from the first fixing member and after a proximal end of a second cord-like member having a distal end fixed to an end of the first fixing member passes through the second fixing member and extends away from the first fixing member, thereby pressing a stopper onto the first cord-like member and placing the first and second living walls between the first and second fixing members, thus holding the living walls clamped together; and a step of pulling the second cord-like member, thereby moving the first cord-like member toward the first fixing member, positioning the first fixing member substantially parallel to the hole, and pulling the first fixing member through the hole into the first organ.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 is a longitudinal sectional view of an instrument for detaining, in patients, the living-wall fixing tool for use with endoscopes, according the first embodiment;

FIG. 8 is a longitudinal sectional view showing the distal part of the insertion section of the instrument incorporated in the living-wall fixing tool for use with endoscopes, according the first embodiment;

FIG. 14 is a perspective view of a modified spacer for the living-wall fixing tool for use with endoscopes, which is the first embodiment;

FIG. 15 is a longitudinal sectional view of the major components, showing the modified spacer incorporated in the living-wall fixing tool for use with endoscopes, which is the first embodiment;

FIG. 22 is a longitudinal sectional view of the major components, showing the second cord being pulled in direction A after the spacer shown in FIG. 14 has been removed from the living-wall fixing tool for use with endoscopes, which is the second embodiment;

FIG. 23 is a perspective view of a modified spacer for the living-wall fixing tool for use with endoscopes, which is the second embodiment;

FIG. 37 is a side view schematically showing the configuration of a living-wall fixing tool for use with endoscopes, according to a fifth embodiment of the present invention;

FIG. 38 is a perspective view depicting the second fixing member of the living-wall fixing tool for use with endoscopes, which is the fifth embodiment;

FIG. 39 is a sectional view, taken alone line 39-39 in FIG. 38;

FIG. 40 is a sectional view, taken alone line 40-40 in FIG. 38;

FIG. 41 is a longitudinal sectional view of the major components, showing the choledochus and duodenum clamped together by the living-wall fixing tool for use with endoscopes, according to the fifth embodiment;

DETAILED DESCRIPTION OF THE INVENTION

Figure 1:
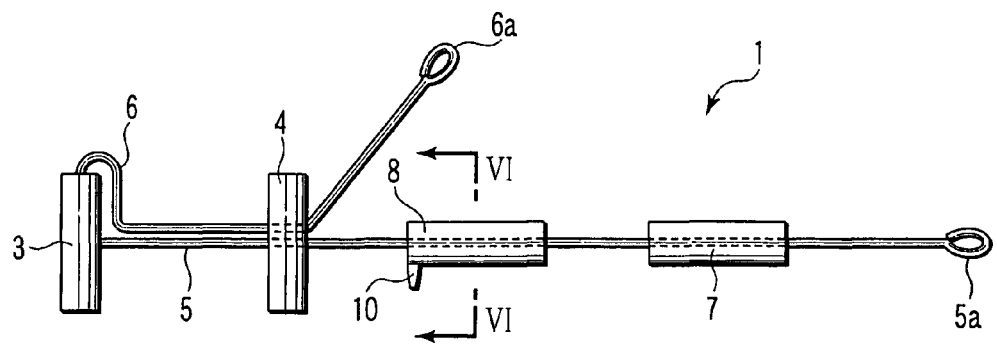
FIG. 1 is a side view schematically showing the configuration of a living-wall fixing tool for use with endoscopes, according to a first embodiment of this invention.

A first embodiment of this invention is described will be described with reference to FIGS. 1 to 3. FIG. 1 shows the configuration of a living-wall fixing tool for use with endoscopes, according to the present embodiment. The living-wall fixing tool 1 is designed for use in forming a stoma that connects, for example, the duodenum H1 (i.e., first organ) and the choledochus. The tool 1 is used to clamp the wall H1a (i.e., first living-wall fixing tool wall, see FIG. 9) of the duodenum and the wall H2a (i.e., second living-wall fixing tool wall, see FIG. 9).

The living-wall fixing tool 1 is guided into the patient's body by using a detention device 2 (see FIG. 7) that is inserted into the patient's body through the channel of an endoscope (not shown). In the patient's body, the tool 1 is detained, clamping the wall H1a of the duodenum H1 and the wall H2a of the choledochus H2.

As FIG. 1 shows, the living-wall fixing tool 1 for use with endoscopes comprises first and second bars 3 and 4, first and second cord-like member 5 and 6, a stopper 7, and a spacer member 8. The first and second bars 3 and 4 are shaft-shaped fixing members. The first and second cord-like member 5 and 6 are cords, which are used in combination with the first and second bars 3 and 4, respectively. The stopper 7 is made of elastic material. The spacer member 8 is a tubular member used as means (later described) for slackening the first cord-like member 5. These components of the living-wall fixing tool 1 for use with endoscopes are made of safe materials that hardly affect living bodies.

Figure 9:
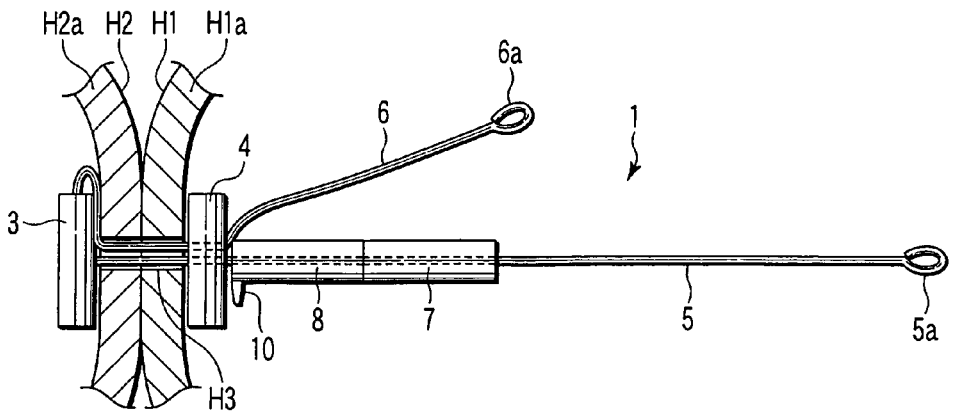
FIG. 9 is a longitudinal sectional view showing the choledochus and the duodenum that are clamped with the living-wall fixing tool for use with endoscopes, according the first embodiment.

As shown in FIG. 9, the first bar 3 is inserted into the choledochus H2 through a through hole H3 made in the junction between the duodenum wall H1a and the choledochus wall H2a. The second bar 4 is arranged inside the duodenum H1, not inserted into the through hole H3. The first bar 3 and the second bar 4 are bar members made of, for example, stainless steel or hard resin such as polycarbonate, polysulfone or polyether ether ketone.

Figure 2:
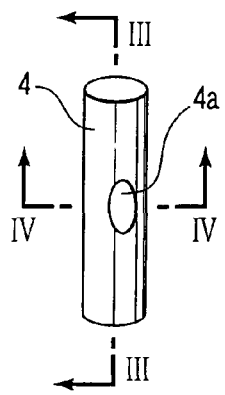
FIG. 2 is a perspective view showing the second fixing member of the living-wall fixing tool-wall, for use with endoscopes, according to the first embodiment.
Figure 3:
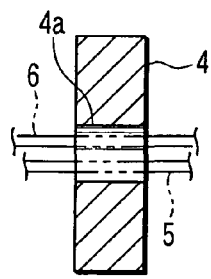
FIG. 3 is a sectional view taken along line III-III in FIG. 2.
Figure 4:
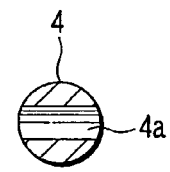
FIG. 4 is a sectional view taken along the line IV-IV in FIG. 2.

As shown in FIGS. 2 to 4, the second bar 4 has an insertion hole 4a in the part that is middle in the axial direction. The cord-like members can pass through insertion hole 4a. The insertion hole 4a extends, intersecting with the axis of the second bar 4 at right angles.

The first cord-like member 5 and the second cord-like member 6 have a distal end part and a proximal distal end part each. They are made of flexible synthetic resin, such as nylon, which has great strength and little elongate. The distal end part of the first cord-like member 5 is secured to that part of the first bar 3, which is almost center in the axial direction thereof. The proximal part of the first cord-like member 5 extends away from the first bar 3 through the insertion hole 4a of the second bar 4. The proximal part of the first cord-like member 5 makes a loop 5a. Instead, the proximal part of the like member 5 may be shaped like, for example, a ball that is easy to hold with hand.

The distal part of the second cord-like member 6 is fastened to the distal end of said first bar 3. The proximal part of the second cord-like member 6 extends away from the first bar 3, through the insertion hole 4a of the second bar 4. A loop 6a is formed at the distal end of the proximal distal end of the second cord-like member 6.

The stopper 7 is a tubular member made of, for example, elastic material such as silicone rubber. The stopper 7 has an inside diameter smaller than the outside diameter of the first cord-like member 5. It has an outside diameter larger than the diameter of the penetration hole 2a made in the first bar 3, i.e., first bar member. The outside diameter of the stopper 7 is larger than the inside diameter of an inner tube 15 (see FIG. 2), which will be described later.

Figure 5:
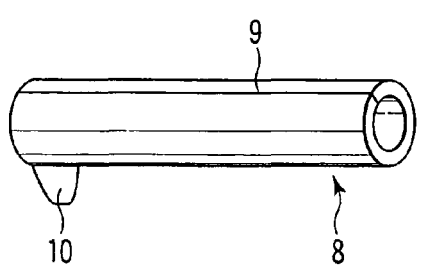
FIG. 5 is a perspective view depicting a spacer for the fixing tool for use with endoscopes, according to the first embodiment.
Figure 6:
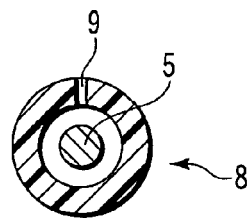
FIG. 6 is a sectional view taken along line VI-VI in FIG. 1.

The spacer member 8 is a bar-like member made of, for example, hard resin such as polycarbonate, polysulfone or polyether ether ketone. As FIG. 5 shows, that tube wall of the spacer member 8 has a slit 9 and a tag 10. The slit 9 extends in the axial direction of the spacer member 8. As shown in FIG. 6, the slit 9 is narrower than the diameter of the first cord-like member 5. The tag 10 is provided at the distal end of the spacer member 8 and protrudes outwards, away from the slit 9.

FIG. 7 shows the detention device 2 for detaining the living-wall fixing tool 1 for use with endoscopes, between two organs in the patient's body. The detention device 2 has an insertion section 12 and a handle section 13.

The insertion section 12 comprises an outer tube 14, an inner tube 15, and a pull wire 16. The outer tube 14 is a flexible tube having such an outside diameter that it can be inserted into the channel of an endoscope. A cap 17 is mounted on the proximal distal end of the outer tube 14. The inner tube 15 is a flexible tube that is inserted in the outer tube 14 and can slide in the outer tube 14. The pull wire 16 is a flexible wire that is inserted in the inner tube 15 and can slide in the axial direction thereof. A hook 16a is attached to the distal end of the pull wire 16.

The handle section 13 has a handle body 18 and a sliding part 19. The proximal distal end of the inner tube 15 is connected to the distal end of the handle body 18. A first handle 20 is provided on the proximal distal end of the handle body 18. The sliding part 19 is inserted in the handle body 18 and can slide in the direction thereof. The proximal distal end of the pull wire 16 is connected with the distal end of sliding part 19. A second handle 21 is provided on the proximal distal end of the sliding part 19.

FIG. 8 shows the living-wall fixing tool 1 for use with endoscopes, incorporated in the distal end portion of the insertion section 12 of detention device 2. As FIG. 8 shows, the hook 16a at the distal end of the pull wire 16 in inner tube 15 holds the loop 5a of the first cord-like member 5 of the tool 1. In this state, the first handle 20 of the detention device 2 may be pulled to the right in FIG. 7. Then, the inner tube 15 retreats to the right, from the distal end of the outer tube 14. The tool 1 is thereby drawn into the distal end part of the outer tube 14 and set in the distal end part of the outer tube 14. As FIG. 8 shows, the first and second cord-like members 5 and 6 are wound, in spiral, around that part of the tool 1 which extends between the first and second bars 3 and 4. The first and second cord-like members 5 and 6 can therefore be packed in the distal end part of the outer tube 14, even if they are longer than is necessary.

How this embodiment operates will be explained. To use the living-wall fixing tool 1 for use with endoscopes, according to this embodiment, an endoscope (not shown) is inserted into the patient through the mouth. The surgeon guides the distal end of the endoscope to the duodenum H1 and set it at a position where the duodenum H1 and the choledochus H2 lie most close to each other, by using, for example, an X ray imaging apparatus or an ultrasonic diagnostic apparatus. If the endoscope used is an ultrasonic-wave endoscope, it is relatively easy to guide the distal end of the endoscope to the desired position.

Then, a puncture needle or a cautery knife is guided to that position through the channel of the endoscope and inserted into the duodenum H1 and the choledochus H2, forming a through hole H3. The through hole H3 is a hole through which the living-wall fixing tool 1 for use with endoscopes will be inserted to clamp the choledochus wall H2a and the duodenum wall H1a together.

The living-wall fixing tool 1 for use with endoscopes is set in the detention device 2 as illustrated in FIG. 8. The insertion section 12 of the detention device 2, which incorporates the tool 1, is inserted into the channel of the endoscope (not shown). At this time, the handle section 13 is arranged outside the channel of the endoscope.

Thereafter, a series of surgical steps (including detention and removal of the tool 1) are performed to clamp the choledochus wall H2a and the duodenum wall H1a by using the fixing tool 1 and the detention device 2. Another surgical step is then performed, forming a stoma in the walls H1a and H2a clamped together and thus making the choledochus H2 and the duodenum H1 communicate with each other. How these surgical steps will be described below.

The handle section 13 and the cap 17 on the outer tube 14 handle are manipulated, moving the insertion section 12 of the detention device 2 forwards through the channel of the endoscope (not shown). Then, the distal end of outer tube 14 is inserted via the through hole H3 into the choledochus H2, to some depth therein.

Then, the handle body 18 (see FIG. 7) is moved forwards, causing the inner tube 15 to advance in the outer tube 14. The first bar 3 of the fixing tool 1 attached at the distal end of the inner tube 15 is thereby pushed out of the outer tube 14.

The first cord-like member 5 and the second cord-like member 6, both lying between the first bar 3 and the second bar 4, are looped, being long enough to enable the first bar 3 to change its posture. Therefore, when the first bar 4 is pushed out of the outer tube 14, the first bar 3 changes in orientation as shown in FIG. 9.

In this state, the outer tube 14 and the handle section 13 are pulled back, moving the insertion section 12 of the detention device 2 back to a position just in front of the duodenum wall H1a.

The handle body 18 is moved forwards from the position to it has retreated. The inner tube 15 is thereby moved forwards, too, until it pushes the second bar 4 of fixing tool 1 out of outer tube 14.

Next, the second handle 21 is pulled toward the proximal end of the tool. As a result, the pull wire 16 is drawn in the inner tube 15, pulling the first cord-like member 5. The stopper 7 stops at the distal end of inner tube 15. As the pull wire 16 is further drawn, the choledochus wall H2a and the duodenum wall H1a are clamped together between the first bar 3 and second bar 4, as shown in FIG. 9.

Next, the cap 17 and the outer tube 14 connected to the cap 17 are retreated. Simultaneously, the handle body 18 and the inner tube 15 connected with the handle body 18 are retreated, too. The sliding part 19 and the wire 16 are relatively moved forwards. As a result, the hook 16a at the distal end of pull wire 16 projects from the distal ends of inner tube 15 and outer tube 14. In this state, the loop 5a is released from the hook 16a. Then, as shown in FIG. 9, the fixing tool 1 is detained in contact with the choledochus wall H2a and the duodenum wall H1a, because of the frictional force of the stopper 7 and the first cord-like member 5.

To form a stoma (not shown) that connects the choledochus H2 to the duodena H1, fixing tools 1 for use with endoscopes are detained in the same way at, for example, two or three positions near the choledochus wall H2a and the duodenum wall H1a. The fixing tools 1 thus positioned are used, clamping the choledochus wall H2a and the duodenum wall H1a together.

Next, a cautery knife is inserted via the channel of the endoscope (not shown). The cautery knife is manipulated, forming a stoma (not shown) in those parts of the duodenum 22 and the choledochus H2, which are clamped with the fixing tools. The stoma thus formed extends from the duodenum 22 to the choledochus H2. The organs thus treated are left for a prescribed time, until those parts of the organs, which have the stoma (not shown), are adhere to each other. Once these parts of the organs adhere to each other, the fixing tools 1 are no longer necessary. Therefore, they are pulled out, as will be explained below.

Figure 10:
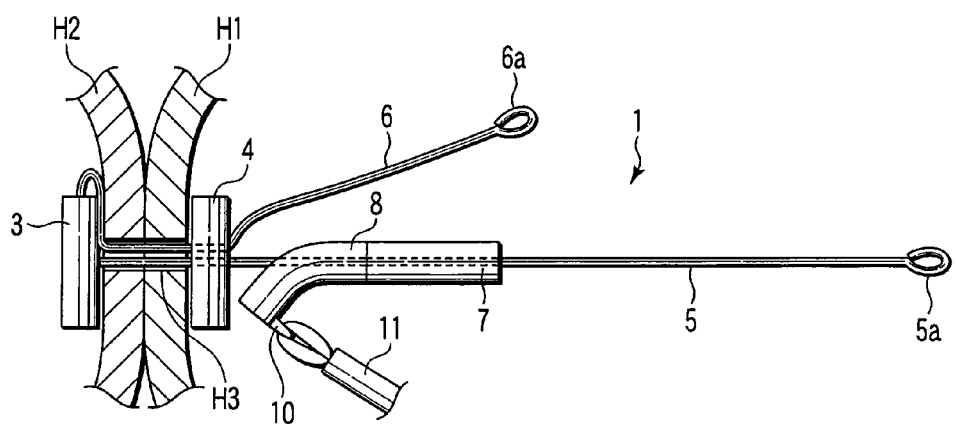
FIG. 10 is a longitudinal sectional view of major components, explaining how a spacer is removed from the living-wall fixing tool for use with endoscopes, which is shown in FIG. 9.
Figure 11:
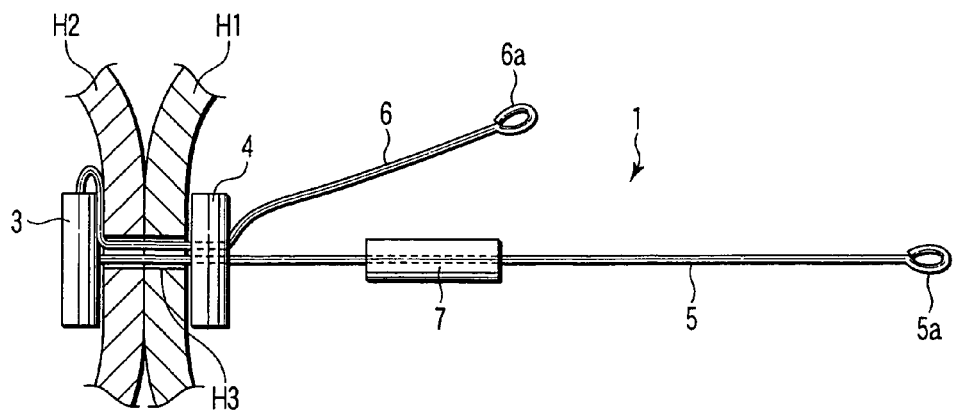
FIG. 11 is a longitudinal sectional view of the major components, not showing the spacer that has been removed from the living-wall fixing tool for use with endoscopes, which is shown in FIG. 9.

To pull out the living-wall fixing tool 1, a grasping forceps 11 is inserted through the channel of the endoscope (not shown) as shown in FIG. 10. The grasping forceps 11 is operated, grasping the tag 10 of spacer member 8. The grasping forceps 11 is pulled, releasing the spacer member 8 from the first cord-like member 5 through the slit 9. A gap is therefore provided between the second bar 4 and the stopper 7, as shown in FIG. 11. As a result, the first cord-like member 5 is no longer pulled. The spacer member 8 is recovered, while being held with the grasping forceps 11.

Figure 12:
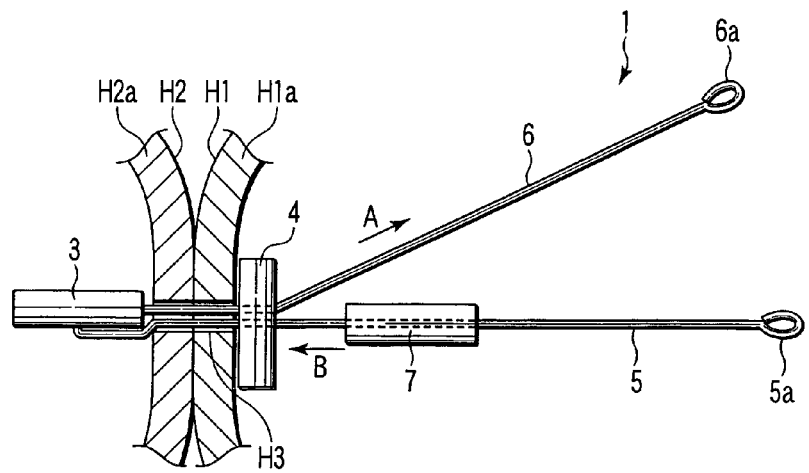
FIG. 12 is a longitudinal sectional view of the major components, showing the second cord being pulled in direction A from the living-wall fixing tool for use with endoscopes, which is shown in FIG. 11.
Figure 13:
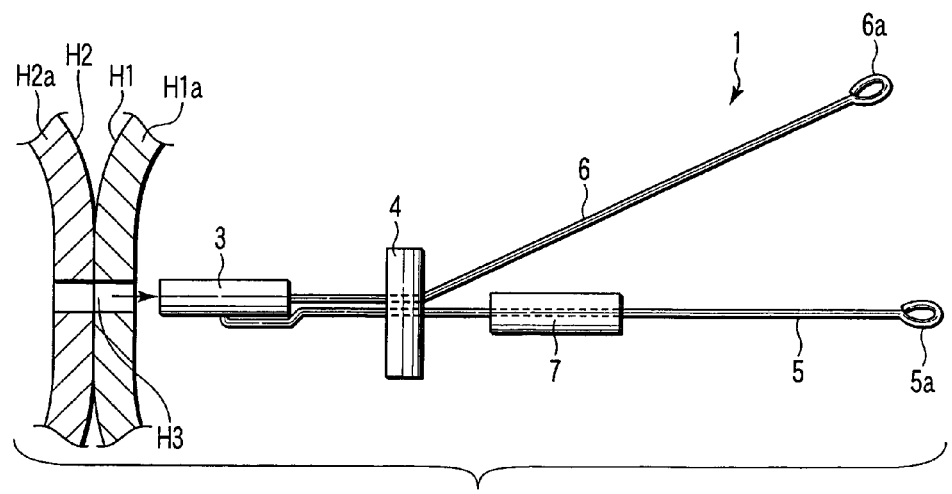
FIG. 13 is a longitudinal sectional view of the major components, explaining how the living-wall fixing tool for use with endoscopes, which is shown in FIG. 12, is pulled from the junction between the choledochus and the duodenum.

Next, the loop 6a of the second cord-like member 6 is pulled toward the proximal end, by using a grasping forceps or the like, as arrow A indicates in FIG. 12. The distal end of the first bar 3 is pulled, by using the second cord-like member 6. As shown in FIG. 12, the first bar 3 is oriented, extending almost perpendicular to the choledochus wall H2a. At this time, the center point on the first bar 3, where the first cord-like member 5 is fixed, moves away from the second bar 4 (that is, toward the distal end). The first cord-like member 5 is therefore pushed toward the distal end, as indicated by arrow B in FIG. 12. More specifically, the first cord-like member 5 is pushed toward the distal end, by only half the length of the first bar 3. Thus, the first bar 3 can easily pass through the hole H3 as shown in FIG. 13. The fixing tool 1 can therefore be pulled out as a whole.

The configuration described above has the following advantages. As indicted above, the fixing tool 1 of FIG. 1 is detained in the patient, by using an endoscope. The tool 1 is then manipulated to clamp the choledochus wall H2a and the duodenum wall H1a. To pull the fixing tool 1 after use, the surgeon holds the tag 10 of the spacer member 8 with the grasping forceps 11. He or she then pulls the tag 10, slackening the first cord-like member 5 through the slit 9 of spacer member 8. That is, the first cord-like member 5 can be loosened as the spacer member 8 is removed. In this state, the loop 6a of the second cord-like member 6 is pulled with the grasping forceps. The first bar 3 is thereby orientated, extending almost perpendicular to the choledochus wall H2a. Therefore, the first bar 3 can easily pass through the hole H3. There is no need to perform a troublesome work such as cutting of the first cord-like member 5 to remove the fixing tool 1. As a result, the fixing tool can be more easily pulled and recovered than in the conventional case where the first cord-like member 5 is cut, slackening it, in order to removed the fixing tool 1 from the patient.

Figure 16:
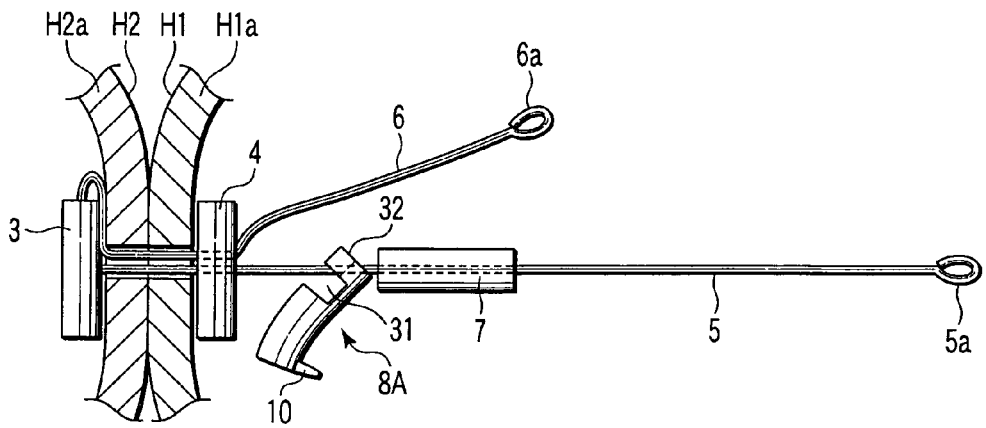
FIG. 16 is a longitudinal sectional view of the major components, explaining how the modified spacer of FIG. 14 is removed from the living-wall fixing tool for use with endoscopes, which is shown in FIG. 15.

FIGS. 14 to 16 show the modification of the first embodiment (see FIGS. 1 to 13). The modified configuration differs from the first embodiment in the structure of the spacer member 8 of the living-wall fixing tool 1 for use with endoscopes, as will be described below.

As shown in FIG. 14, the spacer member 8A has a notch 31 cut in its wall. The spacer member 8A has a ring-shaped part 32 at one distal end near the notch 31. The ring-shaped part 32 ahs no slits 9 at all. To remove the fixing tool 1, the tag 10 of the spacer member 8A is grasped with grasping forceps 11, and the grasping forceps 11 is pulled. Then, the part of the spacer member 8A, other than the ring-shaped part 32, can be released from the first cord-like member 5 through the slit 9 as shown in FIG. 16. The ring-shaped part 32 is left behind, inserted in the first cord-like member 5. Therefore, a part of spacer member 8A can held, coupled to the first cord-like member 5, even if any part other than the ring-shaped part 32 is released from the first cord-like member 5 through the slit 9 at the time of removing the fixing tool 1 and slackens the first cord-like member 5. The spacer member 8A released from the first cord-like member 5 can therefore be recovered together with the fixing tool 1 when the fixing tool 1 is removed from the patient. This makes it even easier to pull the fixing tool 1 as a whole and to recover the same.

FIGS. 17 to 22 show a second embodiment of this invention. This embodiment differs from the first embodiment (see FIGS. 1 to 13) in the structure of the living-wall fixing tool 1 for use with endoscopes is changed as follows.

Figure 17:
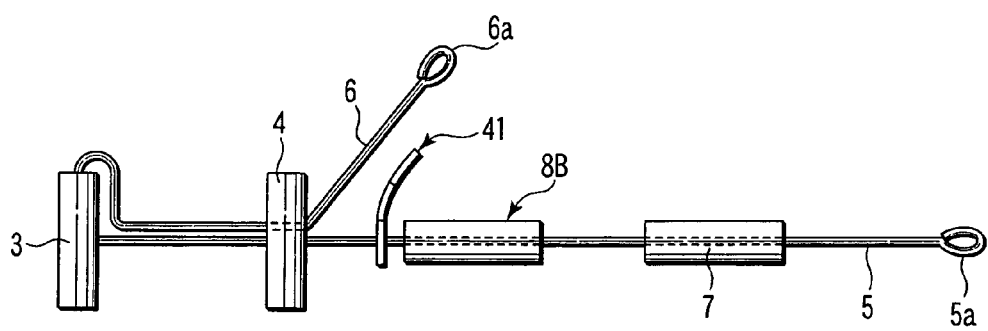
FIG. 17 is a side view schematically showing the configuration of a living-wall fixing tool for use with endoscopes, according to a second embodiment of this invention.
Figure 18:
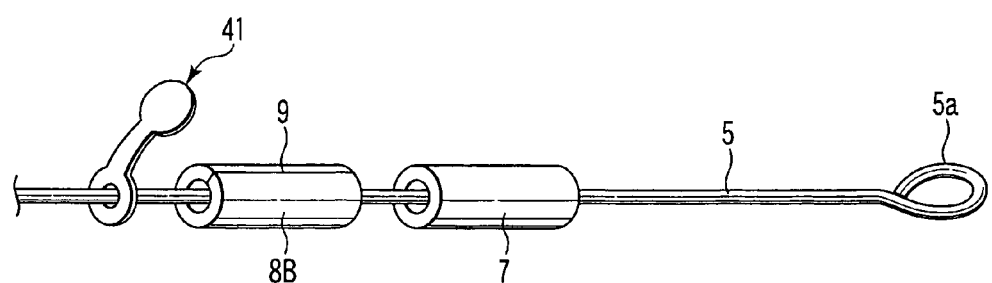
FIG. 18 is a perspective view showing the major components of the living-wall fixing tool for use with endoscopes, according to the second embodiment.
Figure 19:
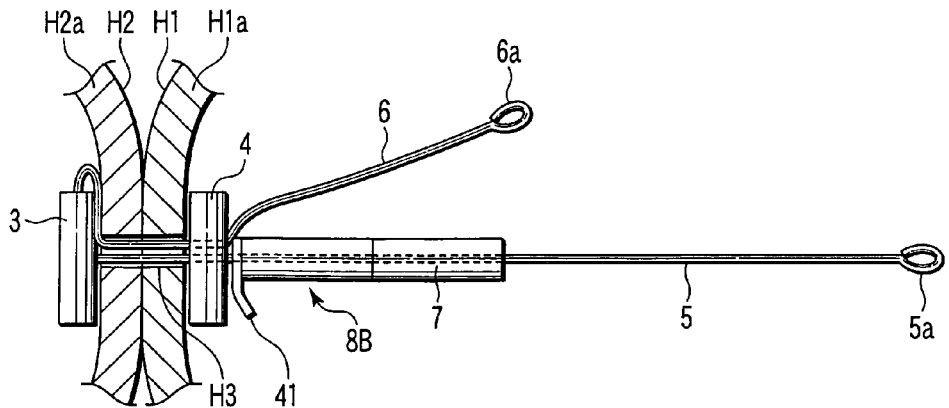
FIG. 19 is a longitudinal sectional view of the major components, showing the choledochus and duodenum clamped together with the living-wall fixing tool for use with endoscopes, according to the second embodiment.

As FIGS. 16 and 17 show, the fixing tool 1 has a tag 41 that is a member separated from the spacer member 8B. That is, the spacer member 8B has no tags, unlike the spacer member 8A of the first embodiment. The tag 41 has a specific color other than those of the living-wall fixing tool tissues in human body, for example green. Therefore, it can be well distinguished from the living tissues.

Figure 20:
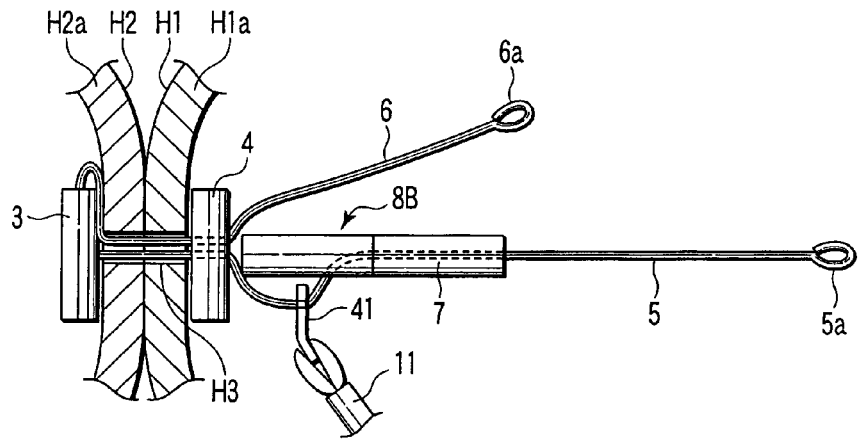
FIG. 20 is a longitudinal sectional view of the major components, explaining how a spacer is removed from the living-wall fixing tool for use with endoscopes, which is shown in FIG. 19.
Figure 21:
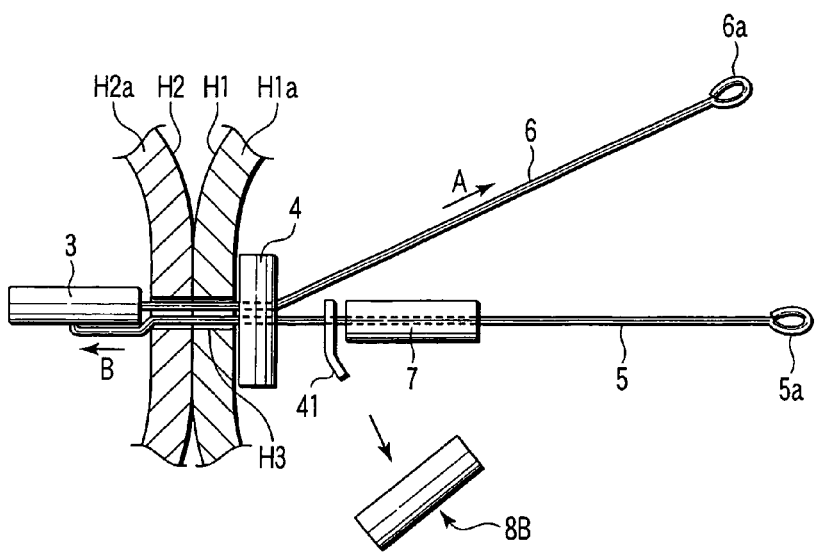
FIG. 21 is a longitudinal sectional view of the major components, showing the second cord being pulled in direction A after the spacer has been removed from the living-wall fixing tool for use with endoscopes, which is shown in FIG. 19.

To remove the fixing 1, the tag 41 is grasped with grasping forceps 11, and the grasping forceps 11 is pulled. Thereby, as shown in FIG. 20, The first cord-like member 5 is thereby released from the spacer member 8B through the slit 9 made in the spacer member 8B. As the spacer member 8B is released, a gap is provided between the second bar 4 and the stopper 7 as shown in FIG. 21. As a result, the first cord-like member 5 is slackened. The spacer member 8B held and removed from the patient by using the grasping forceps 11.

Next, the loop 6a of the second cord-like member 6 is pulled with a grasping forceps or the like, toward the proximal end as arrow A indicates in FIG. 21. The second cord-like member 6 therefore pulls a distal end of the first bar 3. As a result, the first bar 3 is oriented, extending almost perpendicular to the choledochus wall H2a as shown in FIG. 21. At this time, the first cord-like member 5 is pushed from the distal end as indicated by arrow B in FIG. 21. The first bar 3 smoothly passes through the hole H3. Therefore, the fixing tool 1 can be pulled out as a whole.

The configuration described above has the following advantages. In the present embodiment, the fixing tool 1 of FIG. 1 is inserted to the patient through the channel of a endoscope. The fixing tool 1 clamps the choledochus wall H2a and the duodenum wall H1a together. The fixing tool 1 is pulled after use. To remove the tool 1 out of the patient, tag 41, not integral with the spacer member 8B, is grasped and pulled with the grasping forceps 11. The spacer member 8B is thereby released from the first cord-like member 5 through the slit 9 of spacer member 8B. That is, the first cord-like member 5 is loosened as by removing spacer member 8B. In this state, the loop 6a of the second cord-like member 6 is pulled with the grasping forceps. The first bar 3 is thereby oriented, extending almost perpendicular to the choledochus wall H2a. The first bar 3 can therefore easily pass through the hole H3. Therefore, such a troublesome work as cutting the first cord-like member 5 need not be performed in order to remove the fixing tool 1. As a result, the fixing tool can be more easily pulled and recovered than in the conventional case where the first cord-like member 5 is cut, slackening it, in order to removed the fixing tool 1 from the patient.

FIG. 23 shows a modification of the spacer member 8B of the fixing tool 1 for use with endoscopes according to the second embodiment (see FIGS. 17 to 22). The modified spacer member 8B has a guide part 9a at the distal end. The guide part 9a guides the first cord-like member 5 to one distal end of the slit 9. The guide part 9a is defined by tapered surfaces.

The configuration described above achieves the following advantages. As indicated above, the fixing tool 1 is inserted into the patient by using an endoscope. The tool 1 is manipulated, clamping the choledochus wall H2a and the duodenum wall H1a together. To pull out the fixing tool 1 after use, the tag 41, not integral with the spacer member 8B, is grasped and pulled with the grasping forceps 11. At this time, the guide part 9a at one distal end of the slit 9 can reliably guide the first cord-like member 5 to the slit 9. Therefore, after a stoma has been formed and the fixing tool 1, the fixing tool 1, which is foreign matter and no longer necessary, can be easily removed and recovered.

Figure 24:
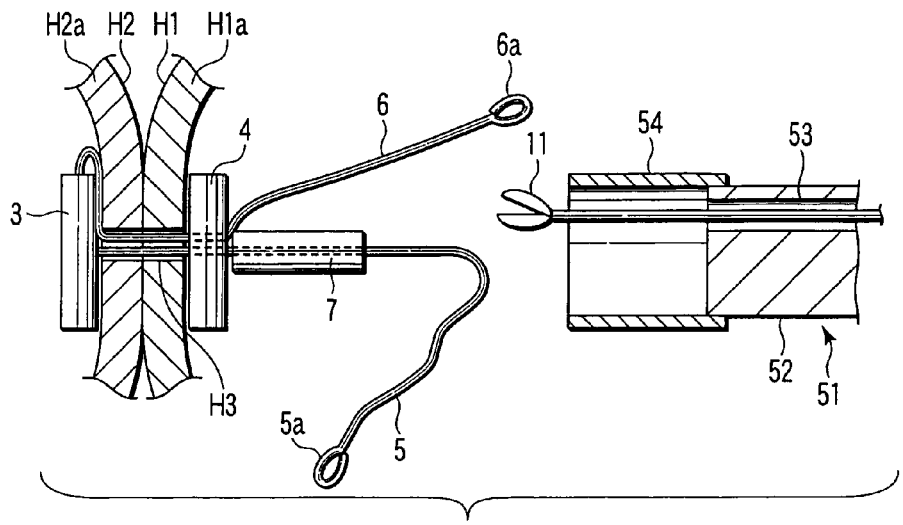
FIG. 24 is a longitudinal sectional view of the major components, showing a living-wall fixing tool for use with endoscopes, which is a third embodiment of this invention, and an endoscope that is used to set and remove the fixing tool.
Figure 25:
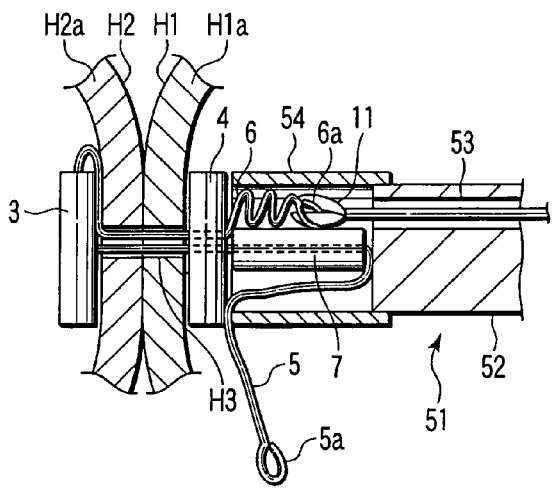
FIG. 25 is a longitudinal sectional view of the major components, showing the endoscope that is set near the living-wall fixing tool for use with endoscopes, which is the third embodiment, in order to remove the living-wall fixing tool.
Figure 26:
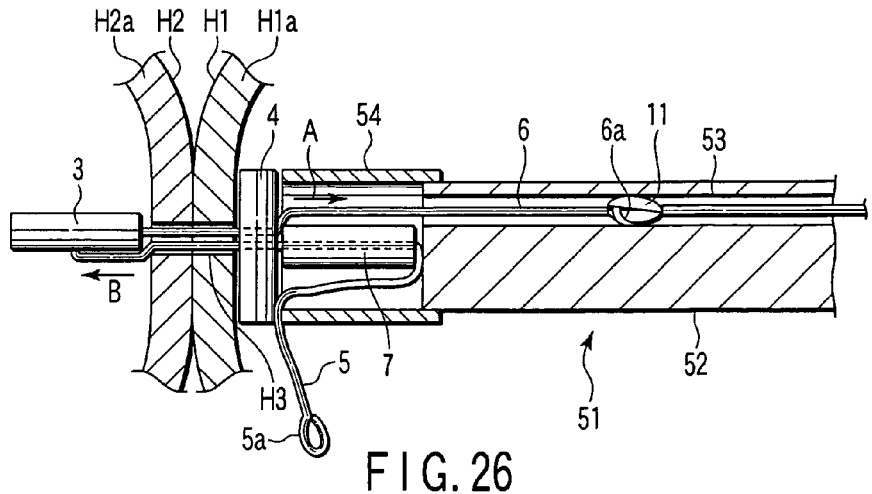
FIG. 26 is a longitudinal sectional view of the major components, showing the second cord being pulled in direction A from the living-wall fixing tool for use with endoscopes, which is the third embodiment and shown in FIG. 25, during the process of removing the living-wall fixing tool.

FIGS. 24 to 26 show a third embodiment of this invention. This embodiment is a living-wall fixing tool 1 for endoscopes, which differs in configuration from the first embodiment (see FIGS. 1 to 13) as follows.

That is, as shown in FIG. 24, the living-wall fixing tool 1 for endoscopes of this embodiment has no component equivalent to the spacer member 8 used in the first embodiment. To remove the fixing tool 1, the first cord-like member 5 can be slackened, only by pulling the loop 6a of the second cord-like member 6 toward the proximal end.

In FIG. 24, reference number 51 designates the endoscope that is used to remove the fixing tool 1. The endoscope 51 has an insertion section 52 and a channel 53 made in the insertion section 52. A grasping forceps 11 is inserted into the channel 53. The distal-distal end part of the insertion section 52 has a cap 54 shaped like a hollow cylinder. The cap 54 need not be attached to the distal-distal end part of insertion section 52. Nevertheless, if the cap 54 is attached to the distal-distal end part of insertion section 52, it will be easier to recognize the view field of the endoscope 51.

It will be described how the living-wall fixing tool 1 for endoscopes of this embodiment is detained in the patient as shown in FIG. 24 and how the fixing tool 1 is pulled from the patient after it has clamped the choledochus wall H2a and the duodenum wall H1a.

First, the grasping forceps 11 is inserted through the channel 53 of the endoscope 51, as is illustrated in FIG. 24. The surgeon grasps the loop 6a of the second cord-like member 6 with grasping forceps 11, while looking at the view field of endoscope 51.

Then, the cap 54 at the distal end of insertion section 52 is made to abut on the second bar 4, as shown in FIG. 25. Thus, the second bar 4 holds the cap 54. In this state, as shown in FIG. 26, the loop 6a of the second cord-like member 6 is pulled with grasping forceps 11, toward the proximal end in the direction of arrow A. Then, the second cord-like member 6 is pulled, pulling the distal end of the first bar 3. The first bar 3 is thereby oriented, almost perpendicular to the choledochus wall H2a, as shown in FIG. 26. At this time, the first cord-like member 5 moves toward the distal end, in the direction of arrow B shown in FIG. 26. The first bar 3 can easily pass through the hole H3. The fixing tool 1 can be therefore pulled out, as a whole.

In this embodiment, the loop 6a of the second cord-like member 6 is held with the grasping forceps 11 and pulled in order to remove the fixing tool 1. At this time, the second cord-like member 6 pulls the first bar 3. So pulled, the first bar 3 is orientated, extending almost perpendicular to the choledochus wall H2a. As the first bar 3 moves so, the first cord-like member 5 can be pushed to the distal end as indicated by arrow B shown in FIG. 26. The first cord-like member 5 can be slackened. Thus, the fixing tool 1 can be loosened as the loop 6a of the second cord-like member 6 is held with the grasping forceps 11 and the second cord-like member 6 is pulled. Once the first bar 3 has been orientated, almost perpendicular to the choledochus wall H2a, the first bar 3 can easily pass along through the hole H3. Therefore, such a troublesome work as cutting the first cord-like member 5 need not be performed to remove the fixing tool 1. As a result, the fixing tool 1 can be more easily pulled and recovered from the patient than in the conventional case where two forceps, i.e., a cutting forceps and a grasping forceps, must be used to cut and slacken the first cord-like member 5 and to remove the fixing tool 1, respectively.

FIGS. 27 to 36 show a fourth embodiment of this invention. This embodiment differs from the living-wall fixing tool 1 for endoscopes, i.e., the first embodiment (see FIG. 1 thru/or 13), as follows.

Figure 27:
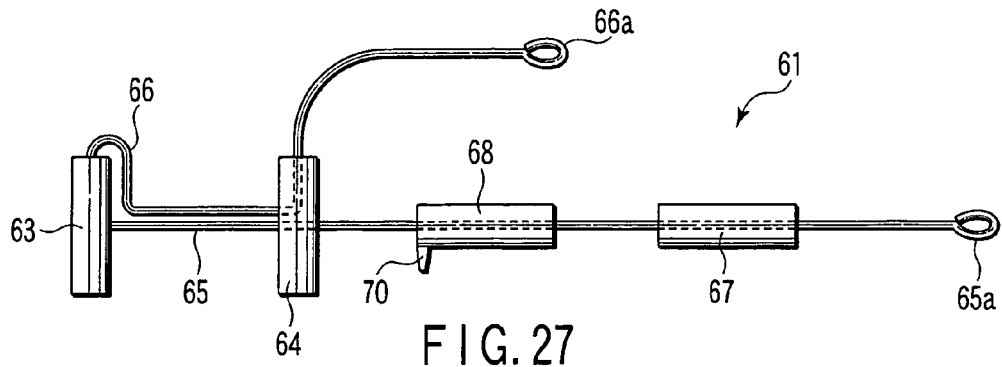
FIG. 27 is a side view schematically showing the configuration of a living-wall fixing tool for use with endoscopes, according to a fourth embodiment of this invention.

As shown in FIG. 27, the living-wall fixing tool 61 for endoscopes, according to this embodiment comprises two fixing members, two cord-like members, and a stopper 67, and a spacer member 68. The two fixing members are first bar 63 and second bar 64 that are shaped like a shaft. The two cord-like members are the first cord-like member 65 and the second cord-like member 66 which are used in combination with the two bars 63 and 64. The stopper 67 is made of elastic material. The spacer member 68 is shaped like a tube and used as means for slackening the first cord-like member 65. The living-wall fixing tool 61 for endoscopes, according to this embodiment, is identical in configuration to the living-wall fixing tool 1 that is the first embodiment, except for the structure of the second bar 64. The spacer member 68 has a slit 9 (see FIG. 5) and a tag 70.

Figure 28:
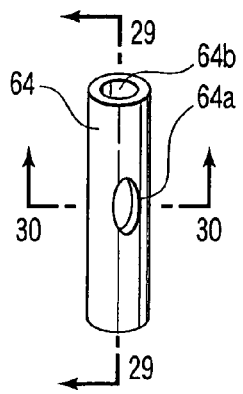
FIG. 28 is a perspective view depicting the second fixing member of the living-wall fixing tool for use with endoscopes, which is the fourth embodiment.
Figure 29:
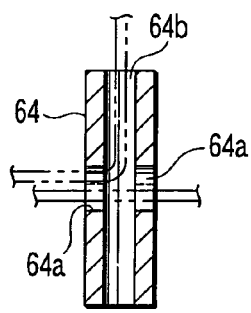
FIG. 29 is a sectional view, taken alone line 29-29 in FIG. 28.
Figure 30:
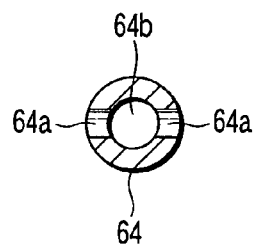
FIG. 30 is a sectional view, taken alone line 30-30 in FIG. 28.

As shown in FIGS. 28-30, the second bar 64 is a tubular member. The second bar 64 has two insertion holes 64a in the middle part, for guiding the two cord-like members. The insertion holes 64a extend at right angles to the axis of the second bar 64. The insertion holes 64a communicate with the channel of the second bar 64.

As FIG. 29 shows, the second cord-like member 66 is inserted, first into the insertion hole 64a of the second bar 64 and then into the other pipe hole 64b of the second bar 64. The second cord-like member 66 finally protrudes from one end of the second bar 64, at the one end of insertion hole 64b.

Figure 31:
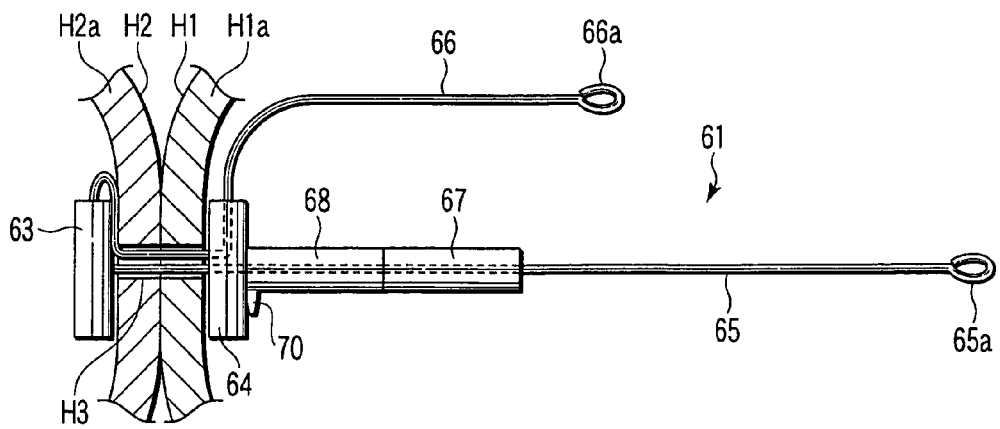
FIG. 31 is a longitudinal sectional view of the major components, showing the choledochus wall and the duodenum wall clamped together by the living-wall fixing tool for use with endoscopes, according to the fourth embodiment.
Figure 32:
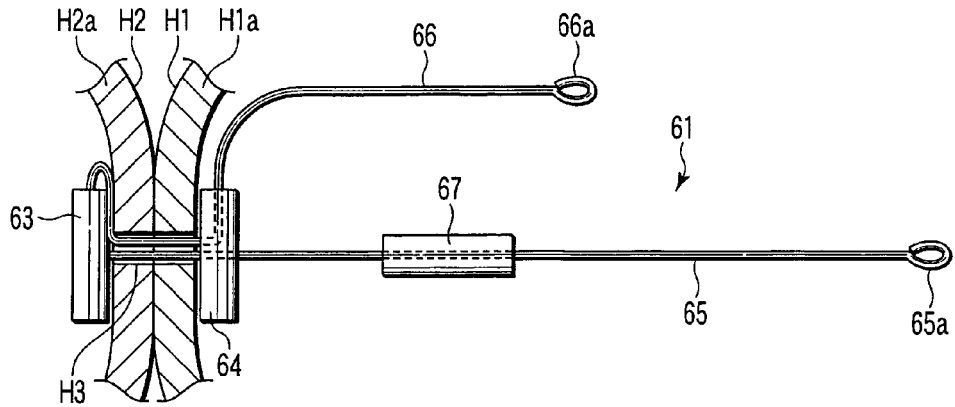
FIG. 32 is a longitudinal sectional view of the major components, showing the living-wall fixing tool of FIG. 31, with the spacer removed from it.

It will be explained how the living-wall fixing tool 61 for endoscopes of this embodiment is detained in the patient as shown in FIG. 31 and is removed from the patient after it has been used to clamp the choledochus wall H2a and the duodenum wall H1a together.

First, as shown in FIG. 10, a grasping forceps 11 is inserted through the channel of an endoscope (not shown). The tag 70 of the spacer member 68 is grasped with the grasping forceps 11. The grasping forceps 11 holding the tag 70 is pulled. The spacer member 68 is thereby released from the first cord-like member 65 through the slit 9 (see FIG. 5). As the spacer member 68 is released, FIG. 32, a gap is provided between the second bar 64 and the stopper 67. As a result, the first cord-like member 65 is slackened. The spacer member 68 is held and recovered by manipulating the grasping forceps 11.

Figure 33:
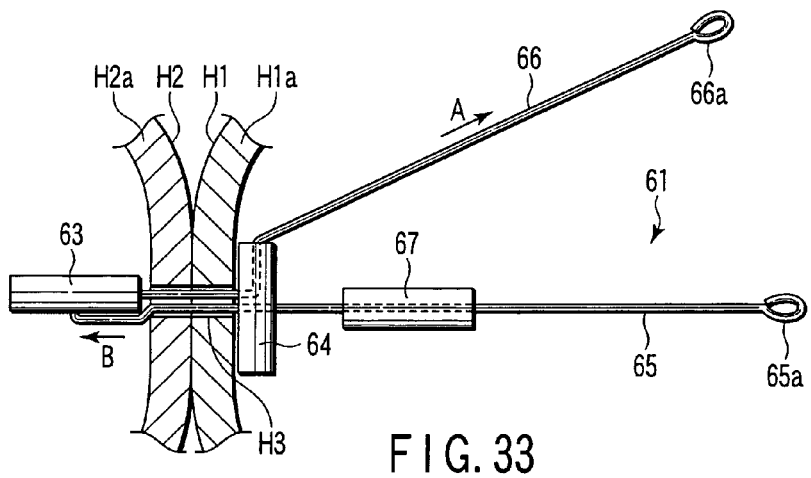
FIG. 33 a longitudinal sectional view of the major components, showing the second cord being pulled in direction A from the living-wall fixing tool for use with endoscopes, which is shown in FIG. 32, during the process of removing the living-wall fixing tool.
Figure 34:
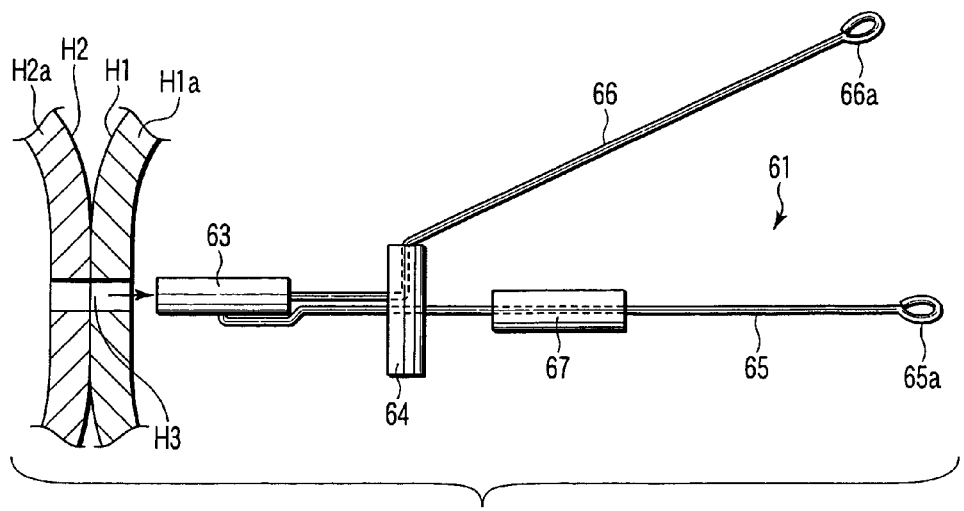
FIG. 34 is a longitudinal sectional view of the major components, explaining how the living-wall fixing tool for use with endoscopes, which is shown in FIG. 32, is pulled from the junction between the choledochus and the duodenum.

Next, the loop 66a of the second cord-like member 66 is pulled with grasping forceps 11, toward the proximal end in the direction indicated by arrow A in FIG. 33. Since the second cord-like member 66 pulls the distal end of the first bar 63, the first bar 63 is orientated, almost perpendicular to the choledochus wall H2a as shown in FIG. 33. At this time, the point on the middle part the first bar 63, at which the central first cord-like member 65 is fixed, is moved away from the second bar 64. Therefore, the first cord-like member 65 is pushed toward the distal end as arrow B indicates in FIG. 33. The first cord-like member 65 is thereby moved toward the distal end, by only half the length of the first bar 63. Thus, the first bar 63 easily passes through the hole H3 as shown in FIG. 34. The fixing tool 61 can be smoothly pulled from the patient.

The configuration described above achieves the following advantages. That is, to remove the fixing tool 61 after it has clamped the choledochus wall H2a and the duodenum wall H1a in the patient, the tag 70 of the spacer member 68 is grasped and pulled with the grasping forceps 11. The spacer member 68 is thereby released from the first cord-like member 65 through the slit 9 (see FIG. 5) of spacer member 68. As a result, the first cord-like member 65 can be slackened. That is, the fixing tool 61 can be loosened by releasing the spacer member 68 from the first cord-like member 65. In this state, the loop 66a of the second cord-like member 66 is pulled to the hand side with grasping forceps 11. The first bar 63 is thereby oriented, extending almost perpendicular to the choledochus wall H2a. The first bar 63 can now easily pass through the hole H3. A troublesome work, such as cutting the first cord-like member 65, need not be performed to remove the fixing tool 61 out of the patient. As a result, the fixing tool 61 can be more easily pulled and recovered, as a whole, from the patient than in the conventional case where two forceps, i.e., a cutting forceps and a grasping forceps, must be used to cut and slacken the first cord-like member 5 and to remove the fixing tool 1, respectively.

Figure 35:
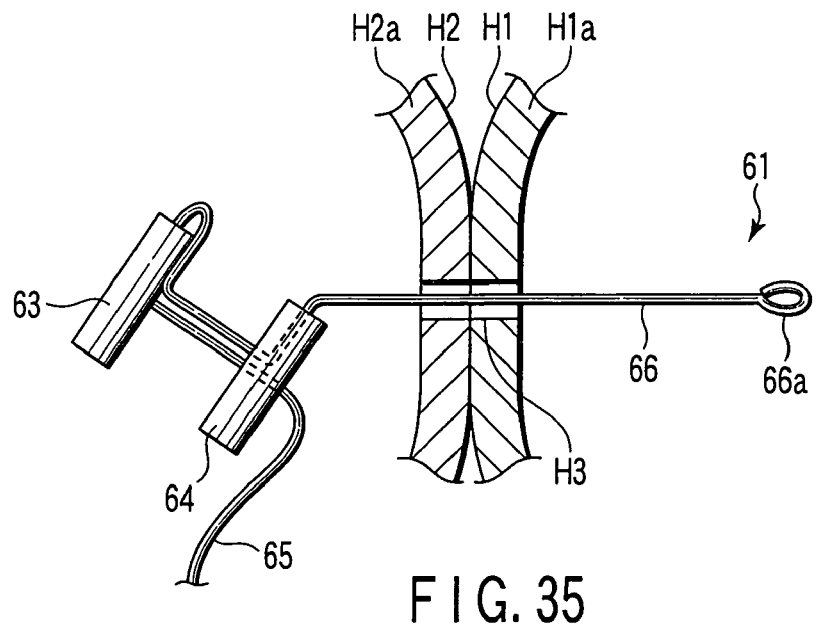
FIG. 35 is a longitudinal sectional view of the major components, showing the living-wall fixing tool for use with endoscopes, i.e., the fourth embodiment, which has been pushed into the choledochus.
Figure 36:
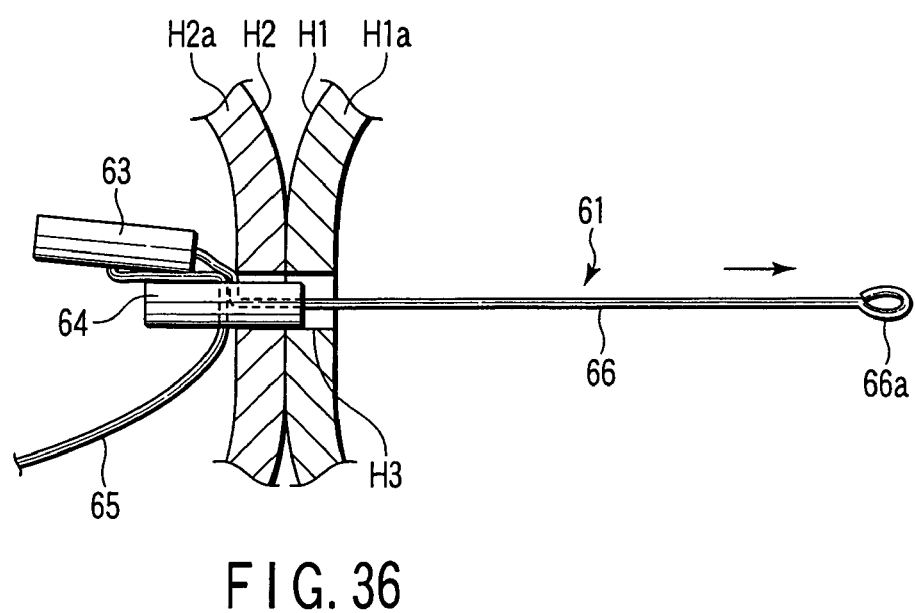
FIG. 36 is a longitudinal sectional view of the major components, explaining how the living-wall fixing tool for use with endoscopes, i.e., the fourth embodiment, is pulled out of the choledochus.

In the present embodiment, the fixing tool 61 may be detained in the choledochus H2 as illustrated in FIG. 35 in order to clamp the choledochus wall H2a and the duodenum wall H1a. In this case, the fixing tool 61 can be easily recovered from the patient. That is, when the loop 66a of the second cord-like member 66 is pulled with the grasping forceps 11 (see FIG. 10) toward the proximal end as shown in FIG. 36, the first bar 63 approaches the second bar 64 and lies parallel thereto. The fixing tool 61 can therefore easily pass through the hole H3. Thus, the fixing tool 61 can be pulled into the duodenum H1.

FIGS. 37 to 43 show a fifth embodiment of this invention. This embodiment differs in configuration from the living-wall fixing tool 1 according to the first embodiment (see FIGS. 1 to 13), as follows.

As FIG. 37 shows, a living-wall fixing tool 71 according to this embodiment comprises a two fixing members, two cord-like members, a stopper 77, and a spacer member 78. The two fixing members are the first bar 73 and the second bar 74. The two cord-like members are the first cord-like member 75 and the second cord-like member 76, which are used in combination with the first and second bars 73 and the second bar 74, respectively. The stopper 77 is made of elastic material. The spacer member 78 is a tubular member that is used means for slackening the first cord-like member 75. The living-wall fixing tool 1 for use with endoscopes, according to the first embodiment, is identical in configuration to the living-wall fixing tool 1 according to the first embodiment, except for the structure of the second bar 74. The spacer member 78 has a slit 9 (see FIG. 5) and a tag 80.

As FIGS. 38 to 40 show, the second bar 74 is a tubular member. The second tube 74 has two insertion holes 74a in the middle part, for guiding the two cord-like members. The insertion holes 74a extend at right angles to the axis of the second bar 74. The insertion holes 74a communicate with the channel 47b of the second bar 74.

As FIG. 39 shows, the second cord-like member 76 is inserted, first into the second bar 74, at one end of the channel 74b thereof, and comes out of the second bar 74, at the other end 74b thereof.

It will be explained how the living-wall fixing tool 71 for use with endoscopes, according to this embodiment, is detained in the patient as shown in FIG. 38, and how the fixing tool 71 pulled after it has clamped the choledochus wall H2a and the duodenum wall H1a together.

Figure 42:
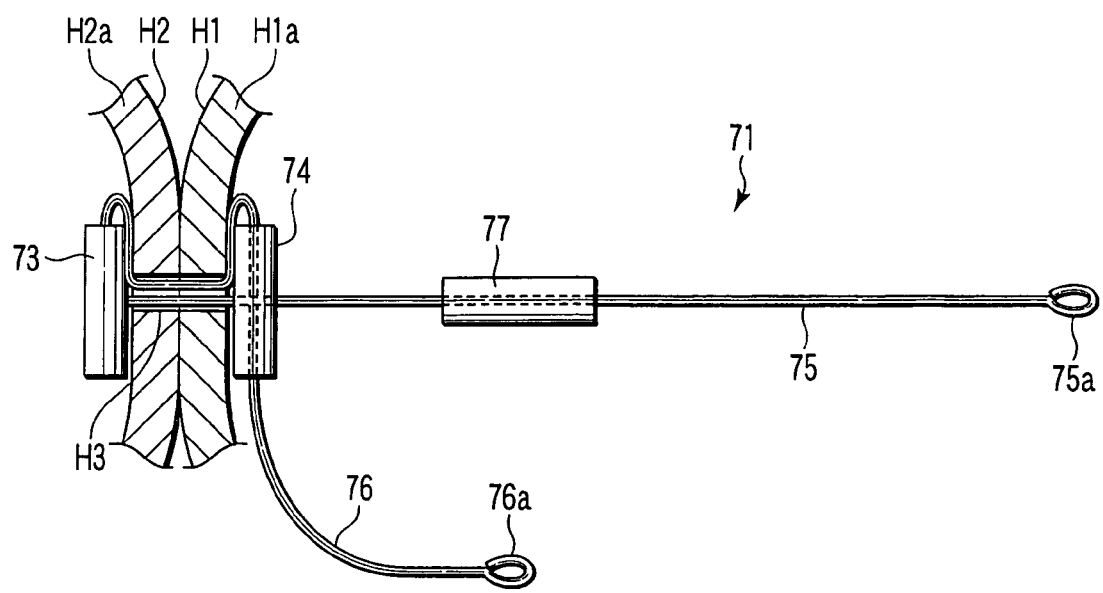
FIG. 42 is a longitudinal sectional view of the major components, showing the living-wall fixing tool, i.e., the fifth embodiment, with the spacer removed from it.

First, as shown in FIG. 10, a grasping forceps 11 is inserted through the channel of an endoscope (not shown). The tag 80 of the spacer member 78 is grasped with the grasping forceps 11. The grasping forceps 11 holding the tag 80 is pulled. The spacer member 78 is thereby released from said first cord-like member 75 through the slit 9 (see FIG. 5). As the spacer member 78 is thus released, a gap is provided between the second bar 74 and stopper 77 as shown in FIG. 42. As a result, the first cord-like member 75 is slackened. The spacer member 78 is grasped and recovered by using the grasping forceps 11.

Figure 43:
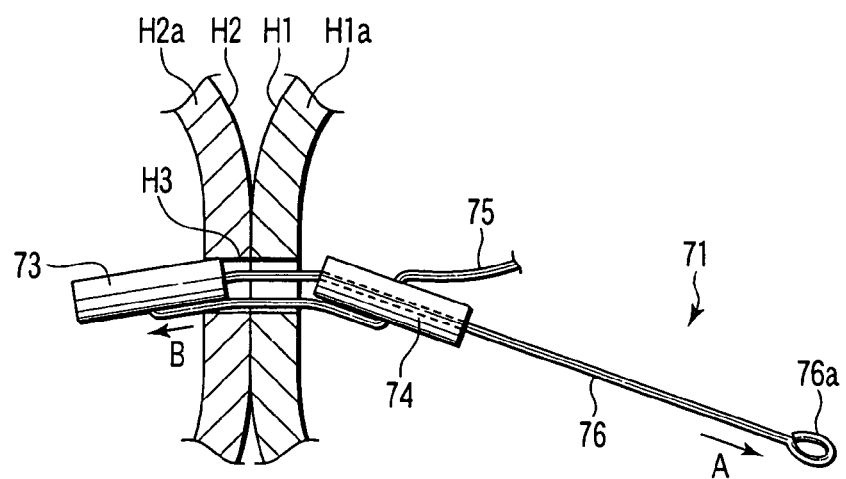
FIG. 43 is a longitudinal sectional view of the major components, showing the second cord being pulled in direction A from the living-wall fixing tool for use with endoscopes, which is shown in FIG. 42, during the process of removing the living-wall fixing tool.

Next, the loop 76a of the second cord-like member 76 is pulled with the grasping forceps 11, toward the proximal end as indicated by arrow A in FIG. 43. The second bar 74 is thereby oriented, extending almost perpendicular to the duodenum wall H1a. Simultaneously, the distal end of the first bar 73 is pulled, the first bar 73 is oriented, thus extending almost perpendicular to the choledochus wall H2a. At this time, the point on the center part of the first bar 73, at which the first cord-like member 75 is fixed, moves away from the second bar 74 (or toward the distal end). Therefore, the first cord-like member 75 is pushed toward the distal end as indicated by arrow B in FIG. 43. Therefore, in this embodiment, the first bar 73 and the second bar 74 are oriented, almost perpendicular to the choledochus wall H2a and the duodenum wall H1a, respectively, when the second cord-like member 76 is pulled. The first bar 73 can easily pass through the hole H3 as shown in FIG. 43. Therefore, the fixing tool 71 can be pulled out as a whole. Note that the first cord-like member 75 must have an extra part whose length is the sum of half the length of the first bar 73 and half the second bar 74.

The configuration described above achieves the following advantages. In this embodiment, the fixing tool 71 for use with endoscopes is detained in the patient. To pull out the fixing tool 71 after it has clamped the choledochus wall H2a and the duodenum wall H1a, the tag 80 of the spacer member 78 is held and pulled with the grasping forceps 11. The spacer member 78 is thereby released from the first cord-like member 75 through the slit 9 (see FIG. 5) of spacer member 78. Thus, the first cord-like member 75 can be slackened. Once the spacer member 78 has been released, the loop 76a of the second cord-like member 76 can be slackened. In this state, the second cord-like member 76 is pulled with grasping forceps 11. Then, the first bar 73 and the second bar 74 are orientated, extending almost perpendicular to the choledochus wall H2a and the duodenum wall H1a, respectively. The first bar 73 and the second bar 74 can then easily pass through hole H3. Therefore, such a troublesome work as cutting the first cord-like member 75 need not be performed to remove the fixed implement 71 from the patient. As a result, the fixing tool 71 can be more easily pulled and recovered than in the conventional case where the first cord-like member 75 is cut, slackening the same, in order to remove the fixing tool 1 from the patient by using two forceps, one for cutting the first cord-like member 75 and the other for grasping the fixing tool 71.

In the present embodiment, too, the fixing tool 71 of FIG. 37 may be detained in the choledochus H2 as in the fourth embodiment (see FIGS. 27 to 36) in order to clamp the choledochus wall H2a and the duodenum wall H1a. In this case, the fixing tool 71 can be easily recovered from the patient. That is, when the loop 76a of the second cord-like member 76 is pulled with the grasping forceps 11 (see FIG. 10), the first bar 73 approaches the second bar 74 are aligned in a straight line. The fixing tool 71 can therefore easily pass through the hole H3. Thus, the fixing tool 71 can be pulled into the duodenum H1, merely by pulling the second cord-like member 76.

Figure 44:
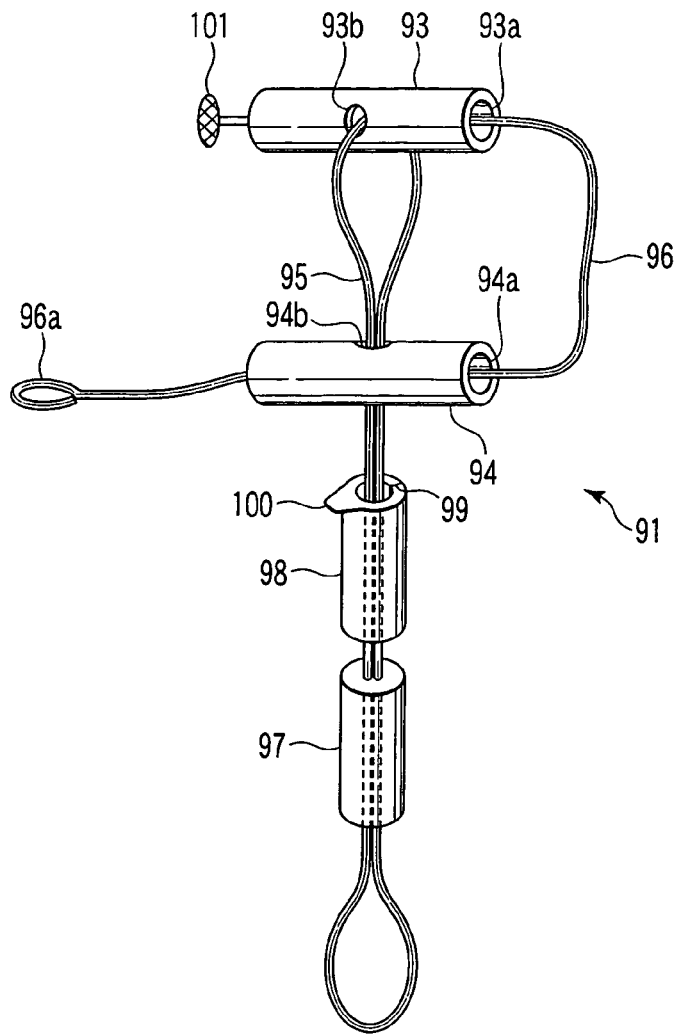
FIG. 44 is a perspective view schematically showing the configuration of a living-wall fixing tool for use with endoscopes, according to a sixth embodiment of this invention.
Figure 45:
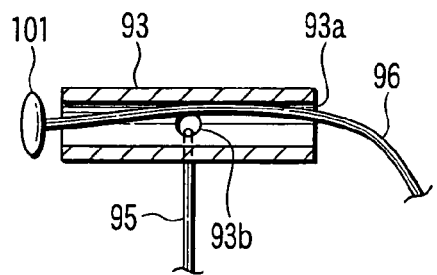
FIG. 45 is a longitudinal sectional view, showing the first and second cords mutually engaged in the living-wall fixing tool for use with endoscopes, which is the sixth embodiment of this invention.
Figure 46:
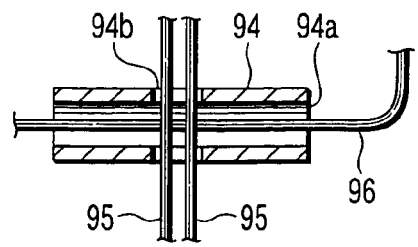
FIG. 46 is a longitudinal sectional view, showing the first and second cords mutually engaged in the living-wall fixing tool for use with endoscopes, which is the sixth embodiment.

FIGS. 44 to 46 show a sixth embodiment of this invention. This embodiment differs from the living-wall fixing tool 1 for endoscopes, according to the first embodiment (see FIGS. 1 to 13) as follows.

The living-wall fixing tool 91 according to this embodiment comprises two fixing members, two cord-like members, and a stopper 97, and a spacer member 98. The two fixing members are first bar 93 and second bar 94 that are shaped like a shaft. The two cord-like members are the first cord-like member 95 and the second cord-like member 96 which are used in combination with the two bars 93 and 94. The stopper 97 is made of elastic material. The spacer member 98 is shaped like a tube and used as means for slackening the first cord-like member 95. The living-wall fixing tool 91 for endoscopes, according to this embodiment, is identical in configuration to the living-wall fixing tool 1 that is the first embodiment, except for the means for fastening the distal end of the first cord-like member 95 bar 93 to the first bar 93 and the means for fastening the distal end of the second cord-like member 96 to the second bar 94. The spacer member 98 has a slit 99 (see FIG. 5) and a tag 100.

The first bar 93 is a tubular member. The second cord-like member 96 extends and can move through the channel 93a of the first bar 93. The distal part of the second cord-like member 96 lies outside the channel 93a of the first bar 93. The second cord-like member 96 has a stopper member 101 at the distal end. The stopper member 101 has a diameter larger than the inside diameter of the first bar 93. When the second cord-like member 96 is pulled, a tension is applied to it. As a result, the stopper member 101 abuts on and is secured to the end of the first bar 93.

As FIG. 45 shows, the first bar 93 has two transverse holes 93b in the middle part. The transverse holes 93b extend at right angles to the axis of the first bar 93. The transverse holes 93b communicate with the channel 93a of the first bar 93.

The first cord-like member 95 is formed of one cord. The first cord-like member 95 extends and can move through the transverse holes 93b of the first bar 93. Two parts of the first cord-like member 95, which protrude from the transverse holes 93a of the first bar 93, extend through the transverse holes 94b of the second bar 94 as shown in FIG. 46. When these too parts of the first cord-like member 95 are pulled, a tension is applied to it. Then, these parts of the first cord-like member 95, which lies in the transverse holes 93a of the first bar 93, pull the first bar 93 toward the proximal end. Fixing means is thus provided, which secures the distal end of the first cord-like member 95 to the first bar 93.

The second bar 94 is a tubular member as ion the fifth embodiment (see FIGS. 37 to 43). The second cord-like member 96 is inserted in the channel 94a of the second bar 94 and can move through the second bar 94.

As FIG. 46 shows, the second bar 94 has two transverse holes 94b in the middle part. The transverse holes 94b extend at right angles to the axis of the second bar 94. The transverse holes 94b communicate with the channel 94a of the second bar 94. Two parts of the first cord-like member 95, which extends protrudes from the transverse holes 93b of the first bar 93, extend through the transverse holes 94b of the second bar 94, respectively. These parts of the first cord-like member 95 pass through the spacer member 98 and then through the stopper 97.

The living-wall fixing tool 91 for endoscopes, according to this embodiment, operates in the same way as the living-wall fixing tool 1 according to the first embodiment (see FIGS. 1 to 13).

The configuration described above achieves the following advantages. In this embodiment, the fixing tool 91 (shown in FIG. 44) for use with endoscopes is detained in the patient. To pull out the fixing tool 91 after it has clamped the choledochus wall H2a and the duodenum wall H1a, the tag 100 of the spacer member 98 is held and pulled with the grasping forceps 11. The spacer member 98 is thereby released from the first cord-like member 95 through the slit 99 (see FIG. 5) of spacer member 98. Thus, the first cord-like member 95 can be slackened. Once the spacer member 98 has been released, the loop 96a of the second cord-like member 96 can be slackened. Thus, the fixing tool 91 can be loosened. In this state, the loop 96a of the second cord-like member 96 is pulled toward the proximal end, by using the grasping forceps 11. The first bar 93 and the second bar 94 are thereby oriented, extending almost perpendicular to the choledochus wall H2a and the duodenum wall H1a, respectively. The first bar 93 and the second bar 94 can therefore easily pass the hole H3. Hence, a troublesome work such as cutting the first cord-like member 95 need not be performed to remove the fixing tool 91. As a result, the fixing tool 91 can be more easily pulled and recovered than in the conventional case where the first cord-like member 95 is cut, slackening the same, in order to remove the fixing tool 1 from the patient by using two forceps, one for cutting the first cord-like member 95 and the other for grasping the fixing tool 91.

This invention is not limited to the embodiments described above. For example, the second bar 4 of the living-wall fixing tool 1 according to the first embodiment (see FIGS. 1 to 13) may be replaced by the second bar 64 of the fourth embodiment (see FIGS. 27 to 36) or by the second bar 74 of the fifth embodiment (see FIGS. 37 to 43).

Further, the second bar 4 of the living-wall fixing tool 1 according to the second embodiment (see FIGS. 17 to 22) may be replaced by the second bar 64 of the fourth embodiment (see FIGS. 27 to 36) or by the second bar 74 of the fifth embodiment (see FIGS. 37 to 43).

Still further, the second bar 4 of the living-wall fixing tool 1 according to the third embodiment (see FIGS. 24 to 26) may be replaced by the second bar 64 of the fourth embodiment (see FIGS. 27 to 36) or by the second bar 74 of the fifth embodiment (see FIGS. 37 to 43). Needless to say, various changes can be made without departing from the scope or spirit of this invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A living-wall fixing tool for use with endoscopes, which is designed to be detained in a living body by using a detention device inserted into the living body through the channel of an endoscope and to clamp the walls of first and second organs in the living body, said endoscope being inserted into the first organ and not inserted into the second organ, said living-wall fixing tool comprising:

first and second fixing members which are shaped like a shaft, the first fixing member being configured to be inserted into the second organ though a hole formed in a junction between a first living wall of the first organ and a second living wall of the second organ, and the second fixing member being configured to be arranged in the first organ, not inserted into the hole;

first and second cord-like members which are to be used in combination with the two fixing members, the first cord-like member having a distal end part connected to the first fixing member and a proximal part extending away from the first fixing member through the second fixing member, and the second cord-like member having a distal end part connected to an end of the first fixing member and a proximal part extending away from the first fixing member through the second fixing member;

an elastic stopper which is slidably mounted on the first cord-like member and which is connected to the first cord-like member when the first cord-like member is pulled, causing the first and second fixing member to clamp the first and second living walls; and slackening means for slackening the first cord-like member, the slackening means being configured to pull, when operated, the second cord-like member to pull the first fixing member into the first organ through the hole.

2. The living-wall fixing tool for use with endoscopes, according to claim 1, wherein the slackening means has a tubular spacer member to be slidably inserted into the first cord-like member, and the spacer member is able to be released from the first cord-like member.

3. The living-wall fixing tool for use with endoscopes, according to claim 2, wherein the spacer member has a slit made in the tube wall and a tag formed on the wall and facing away from the slit, the slit extending in an axial direction of the tube, and the spacer member is released from the first cord-like member through the slit when the tag is pulled.

4. The living-wall fixing tool for use with endoscopes, according to claim 2, wherein the spacer member is at least half as long as the first fixing member as measured in the axial direction of the first fixing member.

5. The living-wall fixing tool for use with endoscopes, according to claim 3, wherein the spacer member has a ring-shaped part that has no slits, at a position in the axial direction of the tube, and the part of the spacer member, other than the ring-shaped part, is able to be released from the first cord-like member through the slit.

6. The living-wall fixing tool for use with endoscopes, according to claim 1, wherein the slackening means has a first cord-fixing part which is located at a middle part of the first fixing member in an axial direction thereof and to which the distal end part of the first cord-like member is fixed, a second cord-fixing part which is located at an end of the first fixing member and to which the distal end of the second cord-like member is fixed, and a cord insertion hole which is made in a middle part of the second fixing member in the axial direction thereof and which extends at right angles to the axial direction of the second fixing member; and the first cord-like member and the second cord-like member extend away from the first fixing member through the cord insertion hole.

7. A living-wall fixing tool for use with endoscopes, which is designed to be detained in a living body by using a detention device inserted into the living body through a channel of an endoscope and to clamp the walls of first and second organs in the living body, said endoscope being inserted into the first organ and not inserted into the second organ, the detention device comprising an insertion section to be inserted into the living body through the channel of the endoscope and a handle section arranged at a proximal end of the insertion section;

the insertion section comprising an outer tube, an inner tube provided in the outer tube and capable of sliding in an axial direction of the outer tube, and an operation wire provided in the inner tube, able to slide in an axial direction of the inner tube and having a hook part at a distal end;

the handle section having an inner-tube operating part which makes the inner tube slide with respect to the outer tube in the axial direction of the outer tube, and a wire-operating part which makes the operation wire slide with respect to the inner tube in the axial direction of the inner tube;

the living-wall fixing tool for use with endoscopes having:

first and second fixing members which are shaped like a shaft, the first fixing member being configured to be inserted into the second organ through a hole formed in a junction between a first living wall of the first organ and a second living wall of the second organ, and the second fixing member being configured to be arranged in the first organ, not inserted into the hole;

first and second cord-like members which are to be used in combination with the two fixing members, the first cord-like member having a distal end part connected to the first fixing member and a proximal part extending away from the first fixing member through the second fixing member, and the second cord-like member having a distal end part connected to an end of the first fixing member and a proximal part extending away from the first fixing member through the second fixing member;

an elastic stopper which is slidably mounted on the first cord-like member and which is connected to the first cord-like member when the first cord-like member is pulled, causing the first and second fixing member to clamp the first and second living walls; and slackening means for slackening the first cord-like member, the slackening means being configured to pull, when operated, the second cord-like member, thereby to pull the first fixing member into the first organ through the hole, the living-wall fixing tool for use with endoscopes being configured to be drawn into the outer tube of the detention device, with the first cord-like member having the distal end engaged with the hook part, and the living-wall fixing tool for use with endoscopes being configured to be pushed from the outer tube as the inner tube of the detention device is pushed, and to clamp the living walls of the first and second organs to each other.

* * * * *